US009993765B2

(12) United States Patent
Galbraith et al.

(10) Patent No.: US 9,993,765 B2
(45) Date of Patent: Jun. 12, 2018

(54) PORTABLE OXYGEN ENRICHMENT DEVICE AND METHOD OF USE

(71) Applicant: SEPARATION DESIGN GROUP LLC, Waynesburg, PA (US)

(72) Inventors: Stephen Douglas Galbraith, Holbrook, PA (US); David K. Walker, Waynesburg, PA (US); Kenneth J. McGowan, Waynesburg, PA (US); Elise N. DePetris, Waynesburg, PA (US); Judith C. Galbraith, Holbrook, PA (US)

(73) Assignee: SEPARATION DESIGN GROUP LLC, Waynesburg, PA (US)

( * ) Notice: Subject to any disclaimer, the term of this patent is extended or adjusted under 35 U.S.C. 154(b) by 33 days.

(21) Appl. No.: 15/248,630

(22) Filed: Aug. 26, 2016

(65) Prior Publication Data
US 2017/0021302 A1 Jan. 26, 2017

Related U.S. Application Data

(60) Continuation of application No. 14/516,919, filed on Oct. 17, 2014, now Pat. No. 9,492,781, which is a
(Continued)

(51) Int. Cl.
*B01D 53/053* (2006.01)
*B01D 53/047* (2006.01)
(Continued)

(52) U.S. Cl.
CPC .......... *B01D 53/0473* (2013.01); *A23L 2/54* (2013.01); *A61K 33/00* (2013.01); *A61L 2/0094* (2013.01);
(Continued)

(58) Field of Classification Search
CPC ............... B01D 53/047; B01D 53/053; B01D 53/0473; B01D 53/0446; B01D 2253/108; B01D 2253/116; B01D 2256/12; B01D 2257/102; B01D 2257/40; B01D 2259/4533; B01D 2259/4541; A23L 2/54; A23V 2002/00; A61K 33/00; A61L 2/0094; A61L 2/22; A61L 9/14; C02F 1/78; C02F 2303/04; A61M 16/10; A61M 16/101;
(Continued)

(56) References Cited

U.S. PATENT DOCUMENTS

| 4,371,384 A | 2/1983 | McCombs |
| 4,440,548 A | 4/1984 | Hill |

(Continued)

FOREIGN PATENT DOCUMENTS

WO   WO-2011/044091 A2   4/2011

OTHER PUBLICATIONS

U.S. Appl. No. 61/527,706, filed Aug. 26, 2011, Galbraith.
(Continued)

*Primary Examiner* — Frank Lawrence
(74) *Attorney, Agent, or Firm* — Panitch Schwarze Belisario & Nadel LLP

(57) ABSTRACT

Lightweight, small, portable devices and methods are disclosed that provide oxygen-enriched air using an ultra rapid adsorption cycle based on advanced molecular sieve materials.

14 Claims, 20 Drawing Sheets

Related U.S. Application Data division of application No. 13/586,223, filed on Aug. 15, 2012, now Pat. No. 8,888,902.

(60) Provisional application No. 61/527,706, filed on Aug. 26, 2011.

(51) Int. Cl.

| | | |
|---|---|---|
| *A61M 35/00* | (2006.01) | |
| *C02F 1/78* | (2006.01) | |
| *A61M 16/10* | (2006.01) | |
| *A23L 2/54* | (2006.01) | |
| *A61K 33/00* | (2006.01) | |
| *F17D 3/01* | (2006.01) | |
| *A61L 2/00* | (2006.01) | |
| *B01D 53/04* | (2006.01) | |
| *A61L 2/22* | (2006.01) | |
| *A61L 9/14* | (2006.01) | |

(52) U.S. Cl.
CPC .......... *A61M 16/10* (2013.01); *A61M 16/101* (2014.02); *A61M 35/00* (2013.01); *B01D 53/047* (2013.01); *B01D 53/053* (2013.01); *C02F 1/78* (2013.01); *F17D 3/01* (2013.01); *A23V 2002/00* (2013.01); *A61L 2/22* (2013.01); *A61L 9/14* (2013.01); *A61M 2205/8206* (2013.01); *A61M 2205/8237* (2013.01); *A61M 2205/8262* (2013.01); *A61M 2205/8293* (2013.01); *A61M 2209/086* (2013.01); *B01D 53/0446* (2013.01); *B01D 2253/108* (2013.01); *B01D 2253/116* (2013.01); *B01D 2256/12* (2013.01); *B01D 2257/102* (2013.01); *B01D 2257/40* (2013.01); *B01D 2259/4533* (2013.01); *B01D 2259/4541* (2013.01); *C02F 2303/04* (2013.01); *Y10T 137/0318* (2015.04)

(58) Field of Classification Search
CPC .. A61M 2205/8206; A61M 2205/8237; A61M 2205/8262; A61M 2205/8293; A61M 2259/086; A61M 35/00; F17D 3/01; Y10T 137/0318
USPC .................. 95/130, 148; 128/204.18, 205.27
See application file for complete search history.

(56) References Cited

U.S. PATENT DOCUMENTS

| | | | | |
|---|---|---|---|---|
| 4,561,865 A * | 12/1985 | McCombs | ........... | B01D 53/053 95/130 |
| 4,725,293 A * | 2/1988 | Gunderson | .......... | B01D 3/0454 96/110 |
| 4,927,434 A * | 5/1990 | Cordes | ................ | B01D 3/0454 95/15 |
| 5,002,591 A * | 3/1991 | Stanford | ................ | B01D 53/04 95/130 |
| 5,154,737 A | 10/1992 | Jenkins et al. | | |
| 5,370,728 A | 12/1994 | LaSala et al. | | |
| 5,388,643 A | 2/1995 | Yee et al. | | |
| 5,522,150 A * | 6/1996 | Schultz | ................ | B60T 17/004 34/80 |
| 5,569,180 A | 10/1996 | Spears | | |
| 5,658,371 A | 8/1997 | Smolarek et al. | | |
| 5,846,294 A | 12/1998 | Doong | | |
| 6,171,371 B1 | 1/2001 | Derive et al. | | |
| 6,183,538 B1 | 2/2001 | Naheiri | | |
| 6,425,938 B1 * | 7/2002 | Xu | ........................ | B01D 53/053 95/100 |
| 6,663,691 B2 | 12/2003 | Yamamoto et al. | | |
| 7,473,299 B2 | 1/2009 | Occhialini et al. | | |
| 7,491,261 B2 | 2/2009 | Warren et al. | | |
| 7,608,132 B2 * | 10/2009 | Fornof | .................. | B60T 17/004 34/79 |
| 7,794,522 B2 | 9/2010 | Bliss et al. | | |
| 8,142,544 B2 | 3/2012 | Taylor et al. | | |
| 8,388,745 B1 | 3/2013 | Pelletier et al. | | |
| 8,496,738 B1 * | 7/2013 | Naheiri | ............... | B01D 53/0476 137/511 |
| 8,888,902 B2 | 11/2014 | Galbraith et al. | | |
| 2002/0029691 A1 | 3/2002 | McCombs et al. | | |
| 2002/0040875 A1 | 4/2002 | Conrad | | |
| 2006/0230931 A1 | 10/2006 | Bliss et al. | | |
| 2007/0169627 A1 * | 7/2007 | Fornof | ............... | B01D 53/0415 96/108 |
| 2007/0227360 A1 | 10/2007 | Atlas et al. | | |
| 2011/0015565 A1 | 1/2011 | Hursey | | |

OTHER PUBLICATIONS

U.S. Appl. No. 13/586,223 (U.S. Pat. No 8,888,902), filed Aug. 5, 2012 (Nov. 18, 2014) Galbraith.

U.S. Appl. No. 14/516,919 (2015-0104524), filed Oct. 17, 2014 (Apr. 16, 2015), Galbraith.

Non-Final Rejection issued by the USPTO dated Apr. 2, 2014 for U.S. Appl. No. 13/586,223, filed Aug. 15, 2012 and published as US 2013-0216627 A1 on Aug. 22, 2012 (Inventors—Galbraith et al.) (12 pages).

Request for Reconsideration submitted to the USPTO dated Aug. 1, 2014 for U.S. Appl. No. 13/586,223, filed Aug. 15, 2012 and published as US 2013-0216627 A1 on Aug. 22, 2012 (Inventors—Galbraith et al.) (25 pages).

Notice of Allowance issued by the USPTO dated Sep. 4, 2014 for U.S. Appl. No. 13/586,223, filed Aug. 15, 2012 and published as US 2013-0216627 A1 on Aug. 22, 2012 (Inventors—Galbraith et al.) (11 page).

Non-Final Rejection issued by the USPTO dated Jul. 14, 2015 for U.S. Appl. No. 14/516,919, filed Oct. 17, 2014 and published as US 2015-0104524 A1 on Apr. 16, 2015 (Inventors—Galbraith et al.) (10 pages).

Response to Non-Final Rejection filed on Dec. 11, 2015 for U.S. Appl. No. 14/516,919, filed Oct. 17, 2014 and published as US 2015-0104524 A1 on Apr. 16, 2015 (Inventors—Galbraith et al.) (16 pages).

Final Rejection issued by the USPTO dated Jan. 8, 2016 for U.S. Appl. No. 14/516,919, filed Oct. 17, 2014 and published as US 2015-0104524 A1 on Apr. 16, 2015 (Inventors—Galbraith et al.) (10 pages).

Response to Final Rejection filed on Jun. 28, 2016 for U.S. Appl. No. 14/516,919, filed Oct. 17, 2014 and published as US 2015-0104524 A1 on Apr. 16, 2015 (Inventors—Galbraith et al.) (9 pages).

Notice of Allowance issued by the USPTO dated Jul. 13, 2016 for U.S. Appl. No. 14/516,919, filed Oct. 17, 2014 and published as US 2015-0104524 A1 on Apr. 16, 2015 (Inventors—Galbraith et al.) (7 pages).

\* cited by examiner

PORTABLE OXYGEN ENRICHMENT DEVICE AND METHOD OF USE

CROSS REFERENCE TO RELATED APPLICATIONS

This application is a continuation of U.S. patent application Ser. No. 14/516,919 filed Oct. 17, 2014, currently pending, which is a divisional application of U.S. patent application Ser. No. 13/586,223 filed Aug. 15, 2012, now issued as U.S. Pat. No. 8,888,902, which claims benefit of U.S. Application No. 61/527,706 filed Aug. 26, 2011, the entire disclosures of which are incorporated herein by reference.

REFERENCE TO GOVERNMENT GRANTS

Portions of the disclosure herein may have been supported in part by grants from the National Science Foundation/Small Business Innovative Research Grant No. 0419821 and the National Institutes of Health/Small Business Technology Transfer Research Grant No. 1 R41 HL080825-01. The United States Government may have certain rights in this application.

FIELD OF THE INVENTION

The invention relates generally to devices, systems, and methods for carrying out adsorption processes for separating and purifying fluid mixtures and, more particularly, to portable devices, systems, and methods for separation and purification processes employing advanced molecular sieve materials, especially for concentrating oxygen for human use.

BACKGROUND OF THE INVENTION

The supply of supplemental oxygen to consumers in homes and other settings is an important and growing segment of the health and leisure industry. Oxygen can be supplied to a user by liquid or compressed oxygen with an appropriate vaporization or pressure regulation system and a gas delivery mechanism. Alternatively, oxygen can be supplied by the generation of oxygen using a small onsite air separation device or medical oxygen concentrator located near the user that delivers the generated oxygen via a cannula or nozzle.

Oxygen concentrators often are preferred over liquid or compressed oxygen supply systems in home, oxygen bar, and fitness center settings and air separation devices for these applications are being repurposed by numerous vendors in the health and fitness field. When portability is required the typical delivery mode is via compression of oxygen enriched air (OEA) in a pressure vessel. Typically canisters are provided that contain 1-8 liters (when measured at standard temperature and pressure) of product that is compressed to between 20 and 150 atmospheres. The highly compressed gas is held in containers made of aluminum, steel, or other suitable material, and is often referred to as "canned oxygen." Unlike medical oxygen, which is delivered continuously or as a bolus triggered by inhalation, supplemental oxygen users typically actuate a valve that releases a 50 to 200 ml burst of OEA, which is directed at the nose and/or mouth during inhalation. Five to 40 bursts per container are typically provided. Various benefits are attributed to the practice of breathing OEA including, but not limited to: increased stamina, reduced fatigue, improved mental acuity and focus, improved complexion, improved general health, and reduced hangovers, jet lag, altitude sickness, headaches, general fatigue, and effects of airborne pollution. As a result, "canned oxygen" or "recreational oxygen" is often used by athletes, city dwellers, business people, alcohol consumers, and others concerned about their general health. While there is not yet strong scientific validation for the claims made by proponents of the casual use of OEA, its use is rapidly increasing as cities become more polluted, stress levels increase, and people become more interested in health and performance issues. Since there are no restrictions on the frequency of use of canned oxygen, it can be overused, causing health and safety issues. Because OEA is typically provided in throw away or refillable containers, there are significant costs attached with the container and shipping. In addition, handling precautions must be observed for the product, which is a combustion accelerant and subject to explosion because the product contents are under high pressure. Also, the use of millions of throw away containers has a negative environmental impact. OEA, when used at high altitudes or to ameliorate the effects of pollution, is typically delivered in continuous mode or at each inhalation.

In addition, it has been found that oxygen or oxygen enriched air can accelerate the healing of flesh wounds and burns. Consequently, health care providers are making wound coverings and oxygen sources available to patients. Currently oxygen is provided via rental of large pressure swing adsorption (PSA) units or undersized electrochemical oxygen producers.

Thus, there is a need to provide an inexpensive, safe, and environmentally sound device and method of delivering OEA. The delivery mode preferably should provide portability, while maintaining the daily volume of OEA that users of canisters and other sources have come to expect, as well as the ability to deliver a comparable bolus of OEA without permitting overuse. There is also a need for a device that can operate in continuous mode, conserver mode, and short burst delivery mode. Also there is a need for a device that can be programmed to vary the volume of delivery relative to time. A need also exists for an inexpensive and small unit that can produce sufficient OEA for wound care therapy. The invention is directed to these, as well as other, important ends.

SUMMARY OF THE INVENTION

The invention provides lightweight, small, portable devices that provide OEA using an ultra rapid adsorption cycle based on advanced molecular sieve materials. The amount of sieve material used to separate air into an oxygen enriched product is a fraction of that used in conventional devices. This dramatically reduces the volume, weight, and cost of the device, and in fact makes the device comparable in size and weight to existing compressed gas devices. Innovations in valve configuration, moisture control, case design, cycle attenuation, and replaceable sieve module are described. Persons desiring portable OEA are provided with a safe, inexpensive, and ecologically sound alternative to containerized OEA. The device produces OEA at purities of up to 95% oxygen and at production levels of 10 to 300 ml per minute. OEA can be delivered continuously or in short duration bursts containing 20 to 400 ml per bolus. OEA oxygen content can be varied between 30% and 95%. Single or dual sieve beds may be employed. When dual sieve beds are used, valve functions may be switched so that the beds may function in standard PSA mode or the beds may be operated in parallel to produce higher product pressure. For wound care uses the output of the device can increase and decrease according to a preset or user determined manner. The use of proprietary 60 to 150 micro meter diameter adsorbent beads allows for ultra fast cycle times and minimum adsorbent inventories. Adsorbent mass may be as little as 2 grams per bed, but is preferentially 5-8 grams per bed. Sieve beds are renewable and easily replaceable if contaminated. Single or multiple sieve beds may be used. A micro controller may be employed to attenuate the adsorb cycle time in order to increase product purity and OEA storage tank pressure. An algorithm relates tank pressure to adsorb time. A battery provides sufficient energy to satisfy a user's daily demands. The device preferably weighs less than 0.5 kilograms and fits into a pocket. Upon shut down the sieve bed(s) and intake passageways are purged with dry product gas to expel possible contaminants. Yearly use cost is a fraction of that of canister provided OEA. Safe operation is assured because OEA is provided and stored at low pressures (typically less than 200 kPa absolute) as compared to canisters at 10,000 kPa. Total volume of accelerant gas is low (typically less than 300 ml) as compared to canisters containing as much as 8000 ml, and maximum possible delivered bolus is limited to typically less than 300 ml compared to the total volume of the canister which may be as much as 8000 ml. Thus dangers due to rupture or explosion are eliminated, shipping requires no special procedures, and the user is protected from possible harmful side effects due to over use.

Accordingly, in one embodiment, the invention is directed devices for oxygen enrichment, comprising:
- a compressor 129;
- an optional air storage vessel 113 having a system purge valve 125;
- at least one pressure swing adsorption unit 111;
- an oxygen purge storage vessel 117;
- an oxygen bolus storage vessel 119 having a pressure sensor 137;
- an optional oxygen delivery button and nozzle assembly 103;
- at least one power source (such as a battery cell 133);
- electronic control unit 131;
- an optional charging port 109;
- a first passageway A connecting said compressor 129 and said air storage vessel 113;
- a second passageway B connecting said air storage vessel 113 and said pressure swing adsorption unit 111;
- a third passageway C connecting said pressure swing adsorption unit 111 and said oxygen purge storage vessel 117;
- a fourth passageway D connecting said oxygen purge storage vessel 117 and said oxygen bolus storage vessel 119;
- a fifth passageway E connecting said oxygen bolus storage vessel 119 and said delivery nozzle 103;
- a first pressure swing adsorption valve 123 associated with said second passageway B, pressure swing adsorption (PSA) unit 111, and exhaust to ambient pressure;
- wherein said first pressure swing adsorption valve is a three-way valve or two two-way valves.
- a restrictor assembly 120 positioned between said pressure swing adsorption unit 111 and said oxygen purge storage vessel 117 and connected to said third passageway C;
- wherein said restrictor assembly is a separate component or part of said pressure swing adsorption unit;
- a check valve/restrictor 135 positioned between said oxygen purge storage vessel 117 and said oxygen bolus storage vessel 119; and
- a delivery valve 127 positioned between said oxygen bolus storage vessel 119 and said delivery nozzle 103.

In certain embodiments of the device, each of said at least one pressure swing adsorption (PSA) unit 111, comprises:
- a housing unit 144 having a feed end F and a product end G;
- at least one input port H for incoming air flow in said feed end;
- at least one output port I for an oxygen-enriched product flow in said product end G;
- an optional rupture plate 143 for said feed end;
- an optional rupture plate 143 for said product end;
- an optional fibrous pad 139 positioned at either end or both ends of said adsorbent bed; and
- at least one adsorbent bed contained in said housing unit, wherein said adsorbent bed comprises at least one molecular sieve material having an average particle size of about 60 μm to 180 μm and having a substantially spherical shape;
- wherein said adsorbent bed has an aspect ratio of length to average width of less than about 10 (preferably, less than about 6).

In certain embodiments of the device, wherein said at least two pressure swing adsorption units 111a, 111b are present and are connected via a multibed product manifold 145;

wherein each of said at least two pressure swing adsorption units comprises:
- a housing unit 144 having a feed end F and a product end G;
- at least one input port H for incoming air flow in said feed end;
- at least one output port I for an oxygen-enriched product flow in said product end G;
- an optional rupture plate 143 for said feed end;
- an optional rupture plate 143 for said product end;
- an optional fibrous pad 139 positioned at either end or both ends of said adsorbent bed; and
- at least one adsorbent bed 111 contained in said housing unit, wherein said adsorbent bed comprises at least one molecular sieve material having an average particle size of about 60 μm to 180 μm and having a substantially spherical shape;
- wherein said adsorbent bed has an aspect ratio of length to average width of less than about 10 (preferably, less than about 6).

In another embodiment, the invention is directed to systems, comprising:
- a device described herein;
- an optional docking station 155;
  - wherein said docking station is optionally capable of performing diagnostic functions;
- an optional computer interface 157 capable of performing diagnostic functions; and
- a battery recharger 108. and
- an optional conserver 159.

In yet other embodiments, the invention is directed to delivery nozzle assemblies 103 for a gas or an aerosol, comprising:
- a delivery valve 127;
- a nozzle 103;
- a delivery passageway 136 connecting said delivery valve 127 to said nozzle 103;

a retaining spring 104 attached to said nozzle 103;
a closable door 128 an optional pivot 106 attached to said closable door 103;
an external activation button 128; and
an optional electrical valve switch 102 capable of activating said delivery valve 127 attached to said external activation button 128.

In further embodiments, the invention is directed to methods, comprising:
compressing an ambient air flow comprising oxygen and nitrogen to form a compressed air flow;
transporting said compressed flow through an adsorbent bed in a device to adsorb at least a portion of said nitrogen to form an oxygen-enriched gas flow;
wherein the pressure drop across said adsorbent bed is less than about 50 kPa; and
wherein said device is portable;
removing said oxygen-enriched gas flow to form an oxygen-enriched product;
transporting said oxygen-enriched product to first vessel and second vessel;
retaining a defined volume of oxygen-enriched product in second vessel'
desorbing from said adsorbent bed said portion of said nitrogen;
purging said adsorbent bed with product gas from first vessel; and
permitting a substantially continuous delivery of a volume of said oxygen-enriched product to a user from second vessel.

In further embodiments, the invention is directed to methods, comprising:
compressing in a device an ambient air flow comprising oxygen and nitrogen to form a compressed air flow;
transporting said compressed flow through an adsorbent bed and adsorbing at least a portion of said nitrogen to form an oxygen-enriched gas flow;
wherein the pressure drop across said adsorbent bed is less than about 50 kPa;
removing said oxygen-enriched gas flow to form an oxygen-enriched product;
transporting said oxygen-enriched product to first vessel and second vessel;
retaining a defined volume of oxygen-enriched product in second vessel;
desorbing from said adsorbent bed said portion of said nitrogen;
purging said adsorbent bed with product gas from first vessel; and
repeating said previous steps until a predetermined pressure is achieved in said second vessel.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE INVENTION

Definitions

Figure 1:
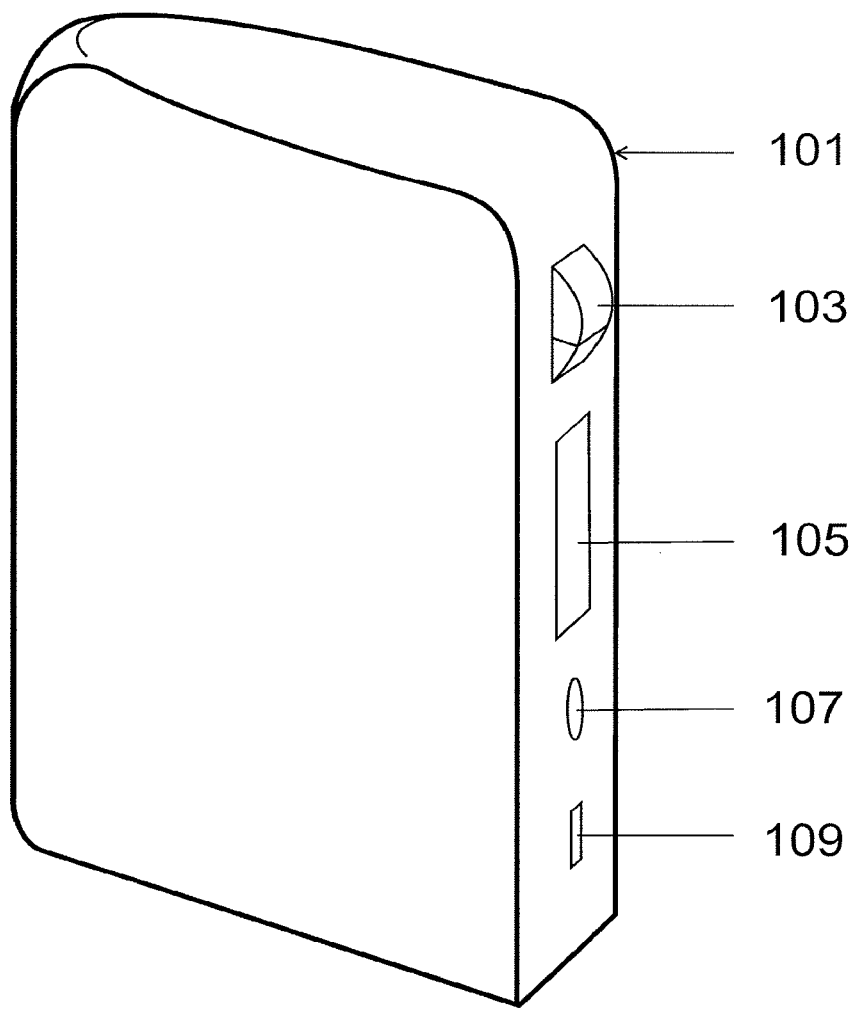
FIG. 1 is a perspective view of one embodiment of the apparatus of the invention.

The following definitions are provided for the full understanding of terms used in this specification.

As used herein, the article "a" means "at least one," unless the context in which the article is used clearly indicates otherwise.

As used herein, the terms "separation" and "separating" mean the act or process of isolating or extracting from or of becoming isolated from a mixture (a composition of two or more substances that are not chemically combined).

As used herein, the terms "purification" and "purifying" means the act or process of separating and removing from anything that which is impure or noxious, or heterogeneous or foreign to it.

As used herein, the term "fluid" refers to a continuous amorphous substance that tends to flow and to conform to the outline of its container, including a liquid or a gas, and specifically includes solutions (where solids dissolved in the liquid or gas) and suspensions (where solids are suspended in liquid or gas).

As used herein, the term "portable" refers to a device that may be capable of being carried or moved. Preferably, the term refers to a device that may be carried by an adult or child with little or no effort. However, the term also refers to a device that is not permanently affixed to a permanent structure and is of sufficiently low mass and bulk that it may be easily transported as part of a vehicle or transportation device. Preferably, the oxygen enrichment devices of the invention weigh less than about 1 kg.

As used herein, the term "chamber" refers to a three-dimensional volume having a generally solid outer surface that is generally elliptical or circular in cross-sectional shape.

As used herein, the term "adsorbent" or "adsorbent contactor" refers to an adsorbent or a membrane containing an adsorbent.

As used herein, the term "oxygen enriched air" or "OEA" refers to air where the level of oxygen has be increased relative to ambient air, preferably at least about a 50% increase, more preferably at least about a 200% increase, and even more preferably at least about a 450% increase.

As used herein, the term "passageway" refers to a way through or along which a substance, such as a liquid, gas, or solid, may pass through one point to another, regardless of length. Examples of passageways include, without limitation, pipes, openings, conduits, and the like.

As used herein, the term "volatile" means that a substance evaporates readily at normal temperatures and pressures.

Reference will now be made in detail to the preferred embodiments of the invention, examples of which are illustrated in the drawings and the examples. This invention may, however, be embodied in many different forms and should not be construed as limited to the embodiments set forth herein. In addition and as will be appreciated by one of skill in the art, the invention may be embodied as a product, method, system or process.

Accordingly, in one embodiment, the invention is directed devices for oxygen enrichment, comprising:
- a compressor 129;
- an optional air storage vessel 113 having a system purge valve 125;
- at least one pressure swing adsorption unit 111;
- an oxygen purge storage vessel 117;
- an oxygen bolus storage vessel 119 having a pressure sensor 137;
- an optional oxygen delivery button and nozzle assembly 103;
- at least one power source (such as a battery cell 133);
- electronic control unit 131;
- an optional charging port 109;
- a first passageway A connecting said compressor 129 and said air storage vessel 113;
- a second passageway B connecting said air storage vessel 113 and said pressure swing adsorption unit 111;
- a third passageway C connecting said pressure swing adsorption unit 111 and said oxygen purge storage vessel 117;
- a fourth passageway D connecting said oxygen purge storage vessel 117 and said oxygen bolus storage vessel 119;
- a fifth passageway E connecting said oxygen bolus storage vessel 119 and said delivery nozzle 103;
- a first pressure swing adsorption valve 123 associated with said second passageway B, pressure swing adsorption (PSA) unit 111, and exhaust to ambient pressure;
- wherein said first pressure swing adsorption valve is a three-way valve or two two-way valves.
- a restrictor assembly 120 positioned between said pressure swing adsorption unit 111 and said oxygen purge storage vessel 117 and connected to said third passageway C;
- wherein said restrictor assembly is a separate component or part of said pressure swing adsorption unit;
- a check valve/restrictor 135 positioned between said oxygen purge storage vessel 117 and said oxygen bolus storage vessel 119; and
- a delivery valve 127 positioned between said oxygen bolus storage vessel 119 and said delivery nozzle 103.

In certain embodiments of the device, each of said at least one pressure swing adsorption (PSA) unit 111, comprises:
- a housing unit 144 having a feed end F and a product end;
- at least one input port H for incoming air flow in said feed end;
- at least one output port I for an oxygen-enriched product flow in said product end G;
- an optional rupture plate 143 for said feed end;
- an optional rupture plate 143 for said product end;
- an optional fibrous pad 139 positioned at either end or both ends of said adsorbent bed; and
- at least one adsorbent bed contained in said housing unit, wherein said adsorbent bed comprises at least one molecular sieve material having an average particle size of about 60 μm to 180 μm and having a substantially spherical shape;
- wherein said adsorbent bed has an aspect ratio of length to average width of less than about 10 (preferably, less than about 6).

In certain embodiments of the device, wherein said at least two pressure swing adsorption units 111a, 111b are present and are connected via a multibed product manifold 145;

wherein each of said at least two pressure swing adsorption units comprises:
- a housing unit 144 having a feed end F and a product end G;
- at least one input port H for incoming air flow in said feed end;
- at least one output port I for an oxygen-enriched product flow in said product end G;
- an optional rupture plate 143 for said feed end;
- an optional rupture plate 143 for said product end;
- an optional fibrous pad 139 positioned at either end or both ends of said adsorbent bed; and
- at least one adsorbent bed 111 contained in said housing unit, wherein said adsorbent bed comprises at least one molecular sieve material having an average particle size of about 60 μm to 180 μm and having a substantially spherical shape;
wherein said adsorbent bed has an aspect ratio of length to average width of less than about 10 (preferably, less than about 6).

In another embodiment, the invention is directed to systems, comprising:
a device described herein;
an optional docking station 155;
wherein said docking station is optionally capable of performing diagnostic functions;
an optional computer interface 157 capable of performing diagnostic functions; and
a battery recharger 108. and
an optional conserver 159.

In yet other embodiments, the invention is directed to delivery nozzle assemblies 103 for a gas or an aerosol, comprising:
a delivery valve 127;
a nozzle 103;
a delivery passageway 136 connecting said delivery valve 127 to said nozzle 103;
a retaining spring 104 attached to said nozzle 103;
a closable door 128 an optional pivot 106 attached to said closable door 103;
an external activation button 128; and
an optional electrical valve switch 102 capable of activating said delivery valve 127 attached to said external activation button 128.

In further embodiments, the invention is directed to methods, comprising:
compressing an ambient air flow comprising oxygen and nitrogen to form a compressed air flow;
transporting said compressed flow through an adsorbent bed in a device to adsorb at least a portion of said nitrogen to form an oxygen-enriched gas flow;
wherein the pressure drop across said adsorbent bed is less than about 50 kPa; and
wherein said device is portable;
removing said oxygen-enriched gas flow to form an oxygen-enriched product;
transporting said oxygen-enriched product to first vessel and second vessel;
retaining a defined volume of oxygen-enriched product in second vessel'
desorbing from said adsorbent bed said portion of said nitrogen;
purging said adsorbent bed with product gas from first vessel; and
permitting a substantially continuous delivery of a volume of said oxygen-enriched product to a user from second vessel.

In further embodiments, the invention is directed to methods, comprising:
compressing in a device an ambient air flow comprising oxygen and nitrogen to form a compressed air flow;
transporting said compressed flow through an adsorbent bed and adsorbing at least a portion of said nitrogen to form an oxygen-enriched gas flow;
wherein the pressure drop across said adsorbent bed is less than about 50 kPa;
removing said oxygen-enriched gas flow to form an oxygen-enriched product;
transporting said oxygen-enriched product to first vessel and second vessel;
retaining a defined volume of oxygen-enriched product in second vessel;
desorbing from said adsorbent bed said portion of said nitrogen;
purging said adsorbent bed with product gas from first vessel; and
repeating said previous steps until a predetermined pressure is achieved in said second vessel.

In certain embodiments of the device, said single adsorbent bed is presented in a folder linear configuration.

In certain embodiments of the device, said adsorbent bed(s) has (have) a total length of no greater than about 15 cm. In certain embodiments of the device, said adsorbent bed has an average width of no greater than about 3 cm.

In certain embodiments of the device, said adsorbent bed is replaceable.

In certain embodiments of the device, said molecular sieve material has an average particle size of about 80 μm to 120 μm.

In certain embodiments of the device, said molecular sieve material has a total mass less than about 10 g.

In certain embodiments of the device, said molecular sieve material comprises zeolite. In certain embodiments of the device, said molecular sieve material comprises a metal-exchanged zeolite. In certain embodiments of the device, said metal-exchanged zeolite is $Li^+$-exchanged zeolite.

In certain embodiments of the device, said restrictor assembly limits flow of product gas during an adsorption period and limits flow of purge gas during a desorption period.

In certain embodiments of the device, said restrictor assembly 120 is an orifice 121, a porous material (122), or a combination thereof.

In certain embodiments of the device, said check valve restrictor assembly 135 comprises a check valve and a flow restrictor.

In certain embodiments of the device, said oxygen bolus storage vessel 119 is fully or partially filled with at least one micro sized material, and restrictors 120 and 135 functions are performed via the flow controlling tortuosity created by the micro sized material.

In certain embodiments of the device, said oxygen bolus storage vessel 119 is fully or partially filled with at least one oxygen selective adsorbent and restrictors 120 and 135 functions are performed via the flow controlling time dependent desorption characteristics of the adsorbent material.

In certain embodiments of the device, said power unit is a battery unit, such as a rechargeable battery unit.

In certain embodiments, the device further comprises a piercing mechanism 124 attached to a product end receiver (sieve access door) 149.

In certain embodiments, the device further comprises a piercing mechanism 124 connected to said first pressure swing adsorption valve 123.

In certain embodiments, the device further comprises a moisture control unit 153 comprising at least one desiccant; wherein said moisture control unit 153 is positioned in said air storage vessel 113 near purge valve 125.

In certain embodiments of the device, said delivery nozzle 103 is retractable. In certain embodiments of the device, said delivery nozzle 103 is retractable and is capable of being simultaneously exposed and activated by a user to deliver oxygen-enriched air.

In certain embodiments, the device further comprises a cannula 130 attached to said delivery nozzle 103. In certain embodiments, the device further comprises a conserver (193) attached to said cannula 130.

In certain embodiments, the device further comprises an antimicrobial substance is present in at least one of said air storage vessel 113; said oxygen purge storage vessel 117; and said oxygen bolus storage vessel 119.

In certain embodiments, the device is portable. In certain embodiments, the device has a mass of less than about 450 g, preferably less than about 350 g.

In certain embodiments, the device is capable of delivering oxygen-enriched product comprising at least about 90% by weight, based on the total weight of said oxygen-enriched product, of oxygen.

In certain embodiments, the device further comprises:
a case 101;
an optional status display 105;
an external control component 107; and
an optional power or charge port 109.

In certain embodiments of the method, the duration of said adsorbing period is increased to about four times the duration of the desorbing period; and the duration of said desorbing remains substantially constant.

In certain embodiments of the method, said user activates said substantially continuous delivery with a cannula or with a user interface button.

In certain embodiments of the method, said oxygen-enriched product comprises at least 30%, by weight, based on the total weight of the oxygen-enriched product, of oxygen and the delivery rate is between about 200 ml per minute and about 400 ml per minute.

In certain embodiments, the method further comprises maintaining the device in a standby mode such that said compressor and valves are not powered when said predetermined pressure is achieved.

In certain embodiments, the method further comprises permitting rapid delivery of said defined volume of said oxygen-enriched product from second vessel as a bolus to a user in a user or device defined frequency.

In certain embodiments of the method, the duration of said adsorbing period lengthens as a function of increasing pressure in said second vessel; and the duration of said desorbing remains substantially constant In certain embodiments of the method, said desorbing occurs after said transporting a defined volume of said oxygen-enriched product to a second vessel.

In certain embodiments, the method further comprises purging said remaining volume of said oxygen-enriched product from said first vessel through said adsorbent bed and air storage vessel upon shutdown.

In certain embodiments of the method, said pressure of said defined volume of said oxygen-enriched product in said second vessel is about 102 kPa absolute to about 200 kPa absolute.

In certain embodiments of the method, the volume of said bolus of said oxygen-enriched product in said second vessel is about 50 cc to about 400 cc at standard temperature and pressure.

In certain embodiments of the method, said defined frequency is about one bolus per minute to about one bolus per three minutes.

In certain embodiments of the method, said bolus of said oxygen-enriched product comprises at least about 90% by weight, based on the total weight of said oxygen-enriched product, of oxygen.

In certain embodiments of the method, said user activates delivery of said defined volume of said oxygen-enriched product as a bolus by pressing a delivery activation button.

In certain embodiments of the method, said device is portable. In certain embodiments of the method, said device has a mass of less than about 450 g, preferably less than about 350 g.

In certain embodiments of the method, said delivery comprises topically treating a wound or a burn with said oxygen-enriched product. In certain embodiments of the method, said wound care oxygen is delivered in a continuous mode. In certain embodiments of the method, said wound care oxygen is delivered in a pressure pulsating mode. In certain embodiments of the method, said wound care oxygen delivery comprises treating a wound or a burn with said oxygen-enriched product in combination with using a gas permeable biologically augmented material as the wound or burn covering. In certain embodiments of the method, said wound care oxygen is delivered in conjunction with a moisturizing or other therapeutic agent.

In certain embodiments, the method further comprises oxygenating a beverage with said oxygen-enriched product.

In certain embodiments, the method further comprises delivering said oxygen-enriched product to a distribution network in a garment, such as a shoe.

In certain embodiments, the method further comprises mixing said oxygen-enriched product with at least one modifying component; wherein said modifying component is volatile; and wherein said modifying component is a material selected from the group consisting of a moisturizing agent, a fragrance, a flavor, an herbal compound, a therapeutic compound, a drug, and combinations thereof.

In certain embodiments, the method further comprises placing a point source of high voltage corona in the oxygen stream to create ozone and delivering said ozone to a microporous distributor for the disinfection of water.

In certain embodiments of the method, said delivery mode is switchable from bolus mode to continuous mode.

To more fully understand the invention, the various embodiments will be described with respect to the figures.

FIG. 1 shows the components assembled into a convenient case 101.

Figure 2:
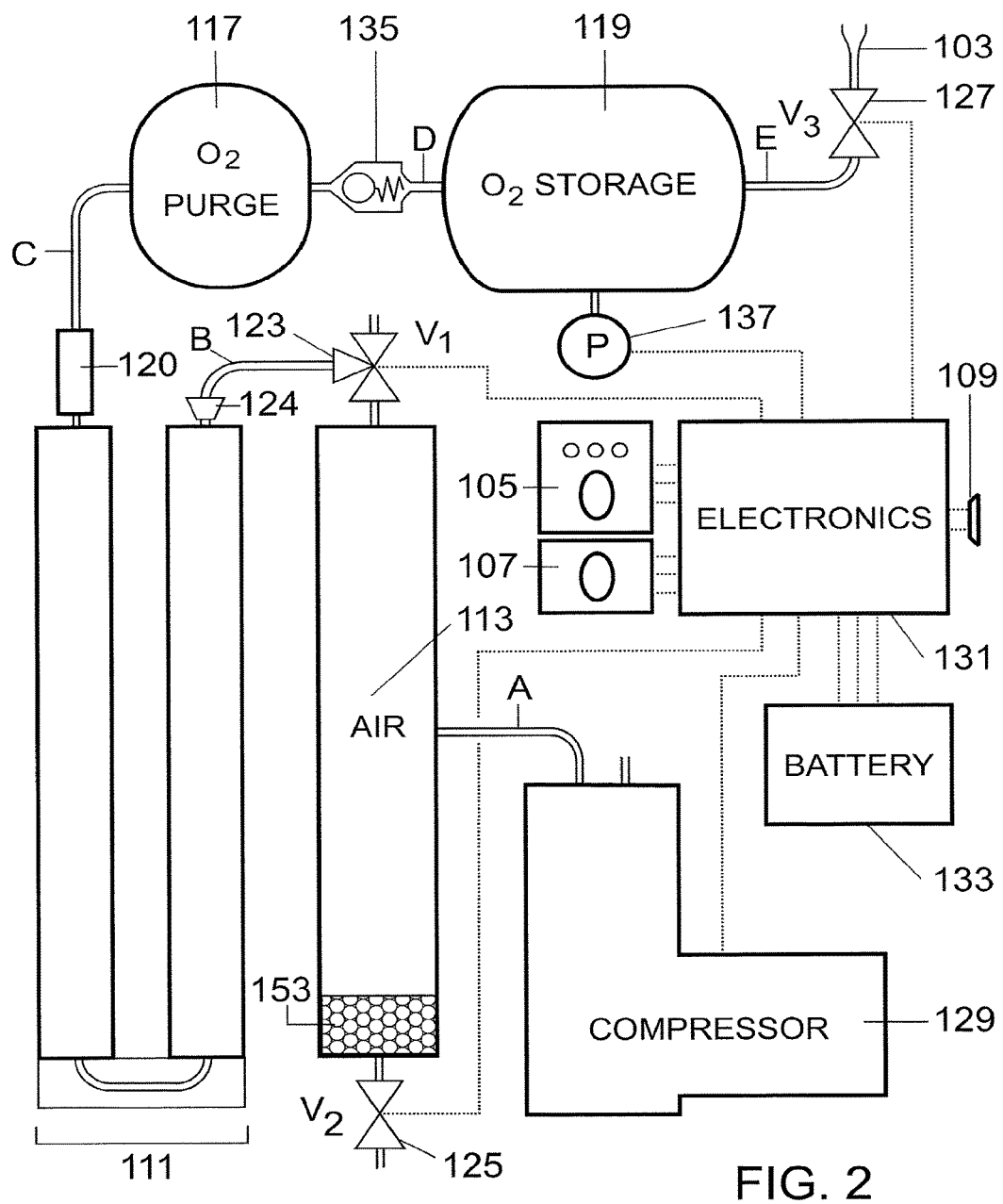
FIG. 2 is a block diagram of the important components of one embodiment of the invention.

FIG. 2 is a block diagram of some of the components of the oxygen concentrator including compressor 129, air storage tank 113, optional desiccant 153, pressure swing adsorption (PSA) valve 123, piercing cone 124, sieve bed assembly 111, optional purge valve 125, flow restrictor 120, oxygen purge tank 117, check valve flow restrictor 135, oxygen storage tanks 119, delivery valve 127, with nozzle 103, pressure sensor 137, user interface and controls 105 and 107, control and power electronics 131, charge port 109, and battery 133.

Figure 8:
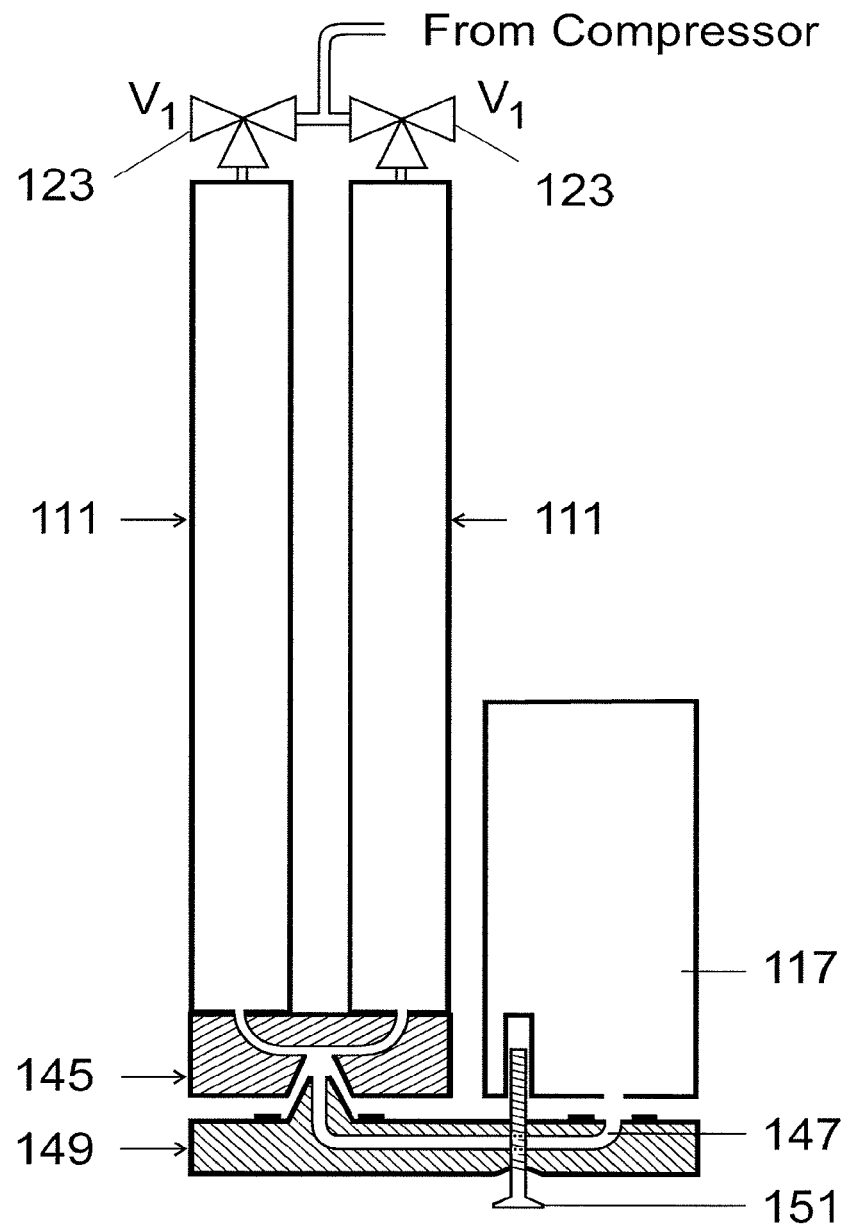
FIG. 8 is a representation of the various components of a replaceable dual sieve bed version of the device.

The removable sieve module 111 may be a dual sieve bed module as shown in FIG. 8 consisting of sieve bed tubular housing 111, flow restrictor 121, connecting manifold 145, retainer door 149, with sealing gaskets 146. Two three-way valves 123 alternately pressurize and exhaust the sieve beds.

Figures 6A, 6B:
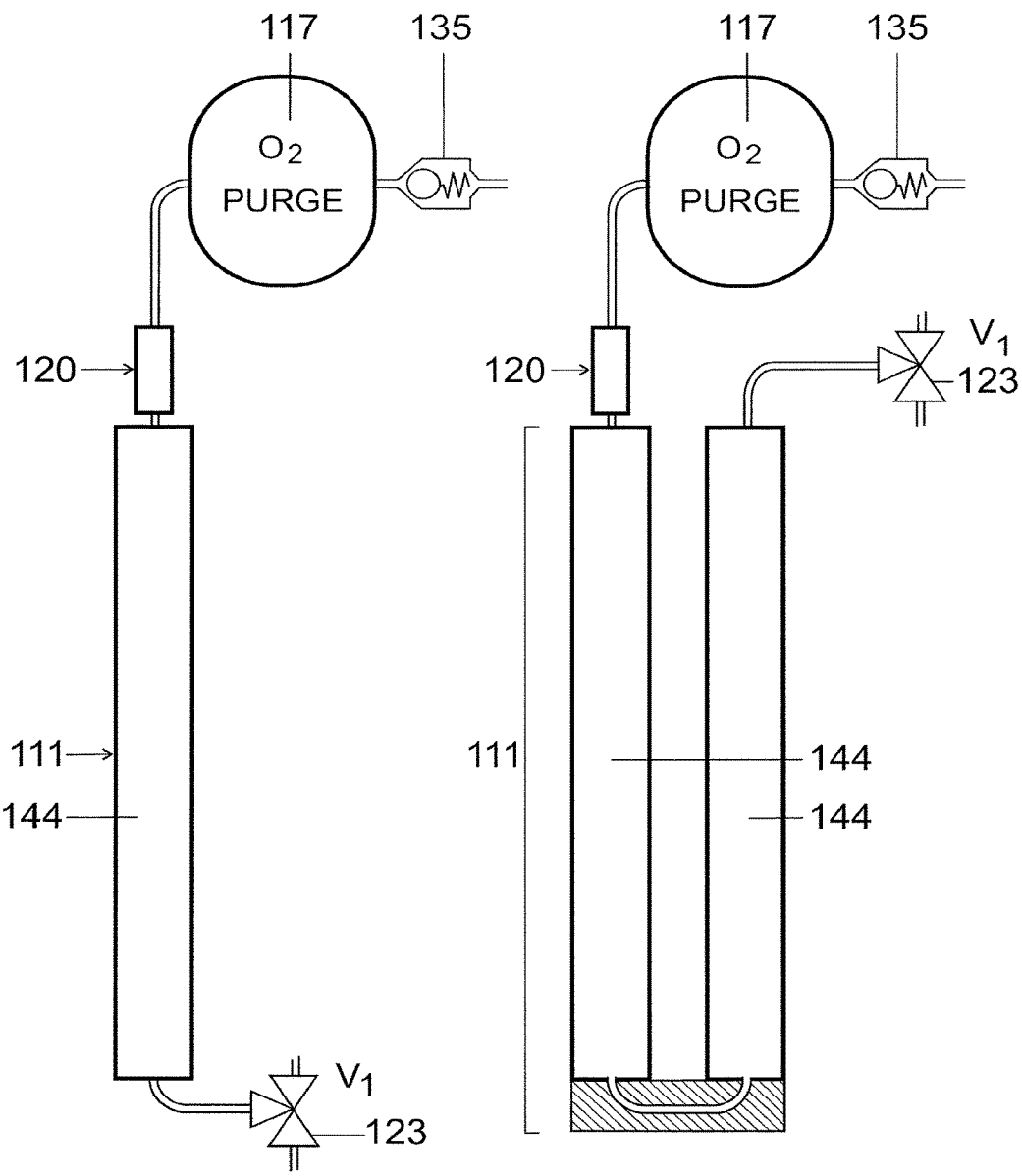
FIG. 6A illustrates a straight bed version of a single sieve bed device of the invention.
FIG. 6B illustrates a folded bed version of a single sieve bed device of the invention.

Alternatively, the sieve bed module may be of the single bed type for simplicity of operation and to reduce cost. FIGS. 6A and B show single sieve beds in straight and folded configurations.

Figure 12A:
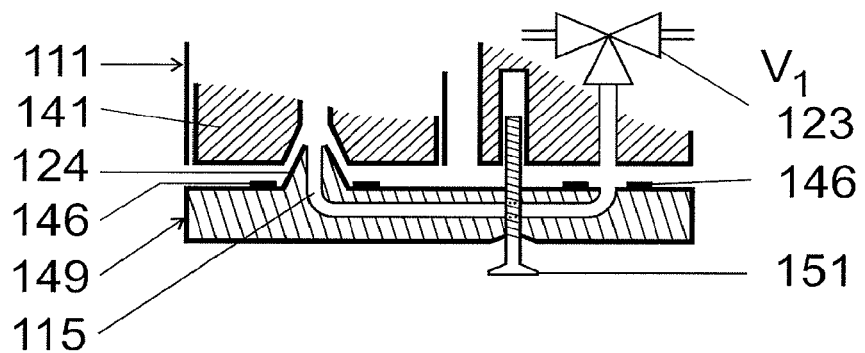
FIG. 12A is a cross-section of the sieve bed retainer door for a single sieve bed device where the door connects to the feed end of the sieve bed.
Figure 12B:
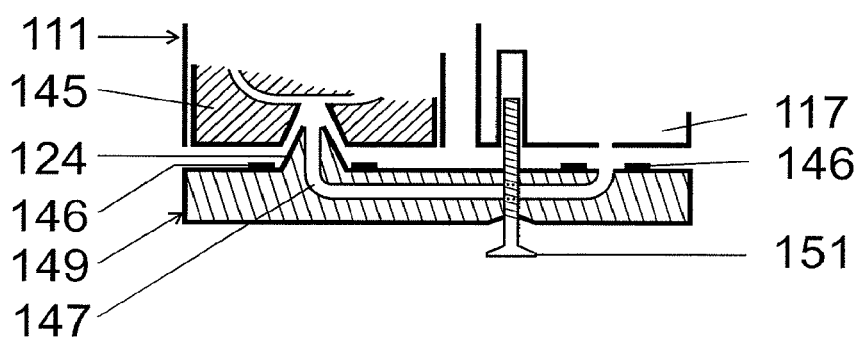
FIG. 12B is a cross-section of the sieve bed retainer door for a single sieve bed device where the door connects to the product end of the sieve bed.

Various replaceable sieve bed retainer door configurations are illustrated in FIGS. 8, 12A and 12B.

The replaceable sieve bed module in one embodiment consists of a single tubular construction 144 having sealable ends 141, puncturable rupture plates 143, an orifice 121 or porous flow restrictor 122, and compressible fibrous pads 139. Ends 141 have conical concavities that act as receivers for conical piercing mechanisms located on the PSA valve manifold 126 and retainer door 149. Passageway 147 forms a pneumatic connection between the sieve bed and the oxygen purge tank 117, as shown in FIG. 12B.

Figure 3A:
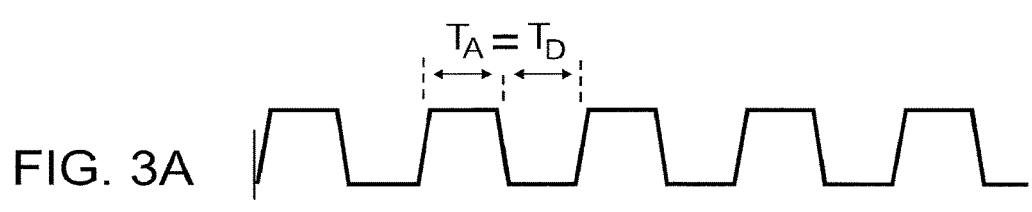
FIG. 3A is a wave form which illustrates adsorb/desorb valve timing for the device operating in continuous mode.

In continuous production mode the device operates as follows. User interface control 105 or 107 signals electronic package 131 to provide power to compressor 129 and to begin a timing sequence that periodically activates three-way valve 123. The compressor delivers air under pressure to storage tank 113 and some moisture is retained in desiccant 153. Valve 123 delivers pressurized air during the adsorptive period to sieve bed assembly 111 that contains highly spherical 80-120μ diameter nitrogen selective beads composed of a binder and lithium exchanged zeolite. Much of the nitrogen is adsorbed and a product gas enriched in oxygen content travels through restrictor 120 into purge tank 117. Restrictor/check valve 135 allows a portion of this product gas to enter oxygen storage tank 119. At the end of the adsorption period valve 123 stops the flow of air from tank 113 and vents the accumulated nitrogen enriched as from sieve bed assembly 111. At the end of this desorption period valve 123 changes position to begin the adsorption period again. The valve timing for this mode of operation is illustrated in FIG. 3A.

When a higher purity product is required, such as for a wound care or ozone application, flow is restricted at nozzle 103 or valve 127 to about 30-60 ml/min. At this flow rate oxygen purities of 85-94% are attainable. If higher flow rates are required, such as for delivery to a cannula or mask for personal health, pollution mitigation, stress relief, or work at high altitude, the valve 127 and nozzle 103 are less restricted and flow rates of about 250-400 ml/min at about 32% oxygen purity are attainable. The purity and flow can be governed either by valve 127, nozzle 103, or by the restrictivity of the delivery component, i.e., the cannula, the tubing, or the mask, or by changing the PSA valve timing.

Figure 3B:
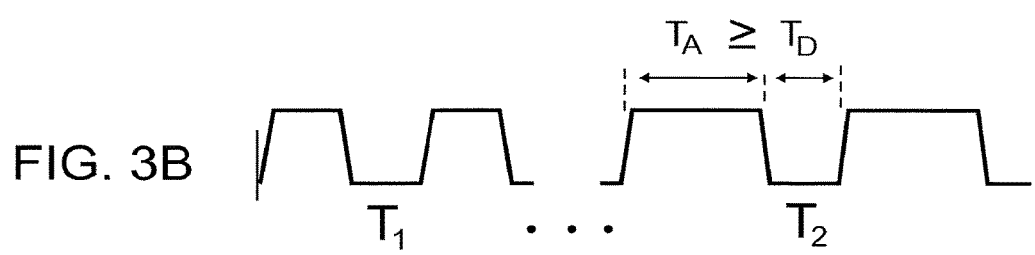
FIG. 3B is a wave form which illustrates adsorb/desorb valve timing. $T_1$ at beginning of bolus mode and $T_2$ at end of pulse dose mode.
Figure 5:
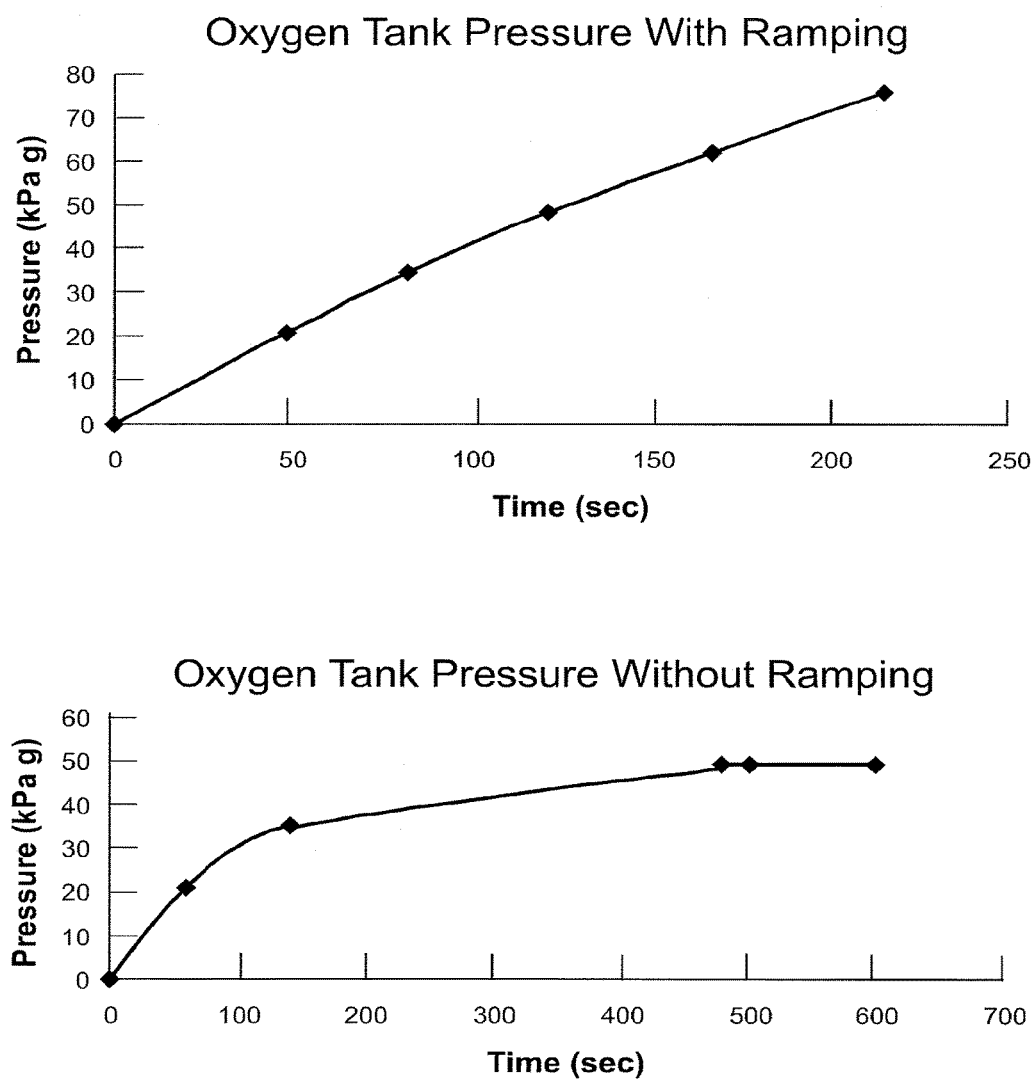
FIG. 5 is a graph which shows how ramping affects product oxygen purity and pressure.
Figure 9A:
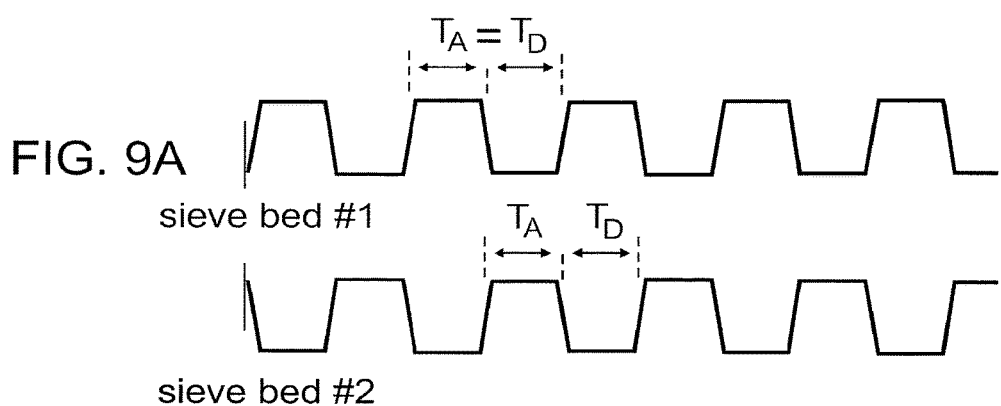
FIG. 9A is a wave form which represents the valve timing functions of a dual sieve bed device in continuous mode.
Figure 9B:
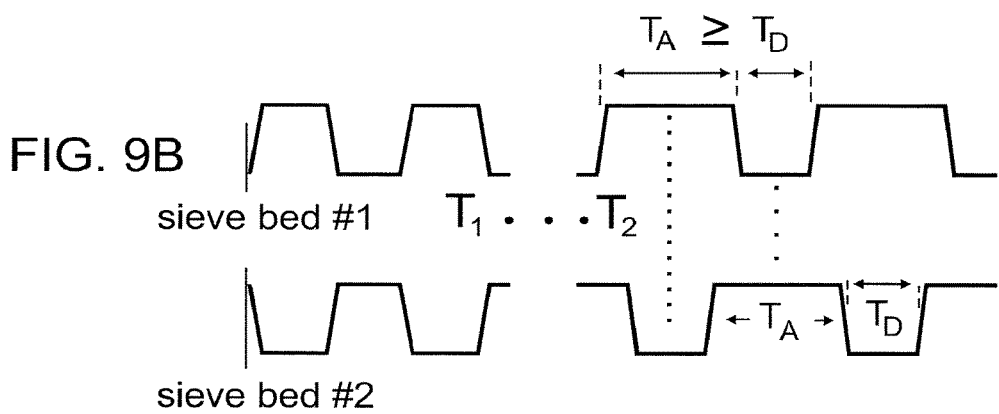
FIG. 9B is a wave form which represents the variable valve timing functions of a dual sieve bed device in bolus mode.

In bolus delivery mode the object is to manufacture and store a predetermined quantity of higher purity oxygen that can be used at the user's discretion. The operation is different than the continuous mode operation in that (1) delivery valve 127 remains in the closed position allowing storage tank 119 to pressurize; and (2) the adsorption time increases as oxygen storage tank 119 pressure increases. This is represented in FIG. 3B where $T_1$ is pressurization begin time and $T_2$ is pressurization end time. An experimentally derived algorithm relates adsorb time to storage tank pressure. FIG. 5 illustrates how ramping the adsorb timing affects the product purity and the time required to pressurize the product vessel. In one embodiment of the invention 3 minutes and 10 seconds are required to produce a bolus of 90% purity oxygen that has a volume of 130 ml (STP). FIGS. 9A and 9B illustrate the dual sieve bed valve timing in continuous (9A) and bolus (9B) modes of operation. When the predetermined pressure is achieved in tank 119 the device goes into shut down or hibernate mode and the compressor and valve 123 operations cease. In hibernate mode the bolus of oxygen is available to the user and when valve 127 is activated the stored oxygen is delivered through nozzle 103 for inhalation by the user.

Oxygen purge tank 117 provides a significant quantity of product gas to purge the system during the desorb cycle and fill the sieve bed with product gas in preparation for the next adsorb cycle. Check valve/restrictor 135 prevents product gas in storage tank 119 from being used during the desorb/purge cycle.

Figure 10:
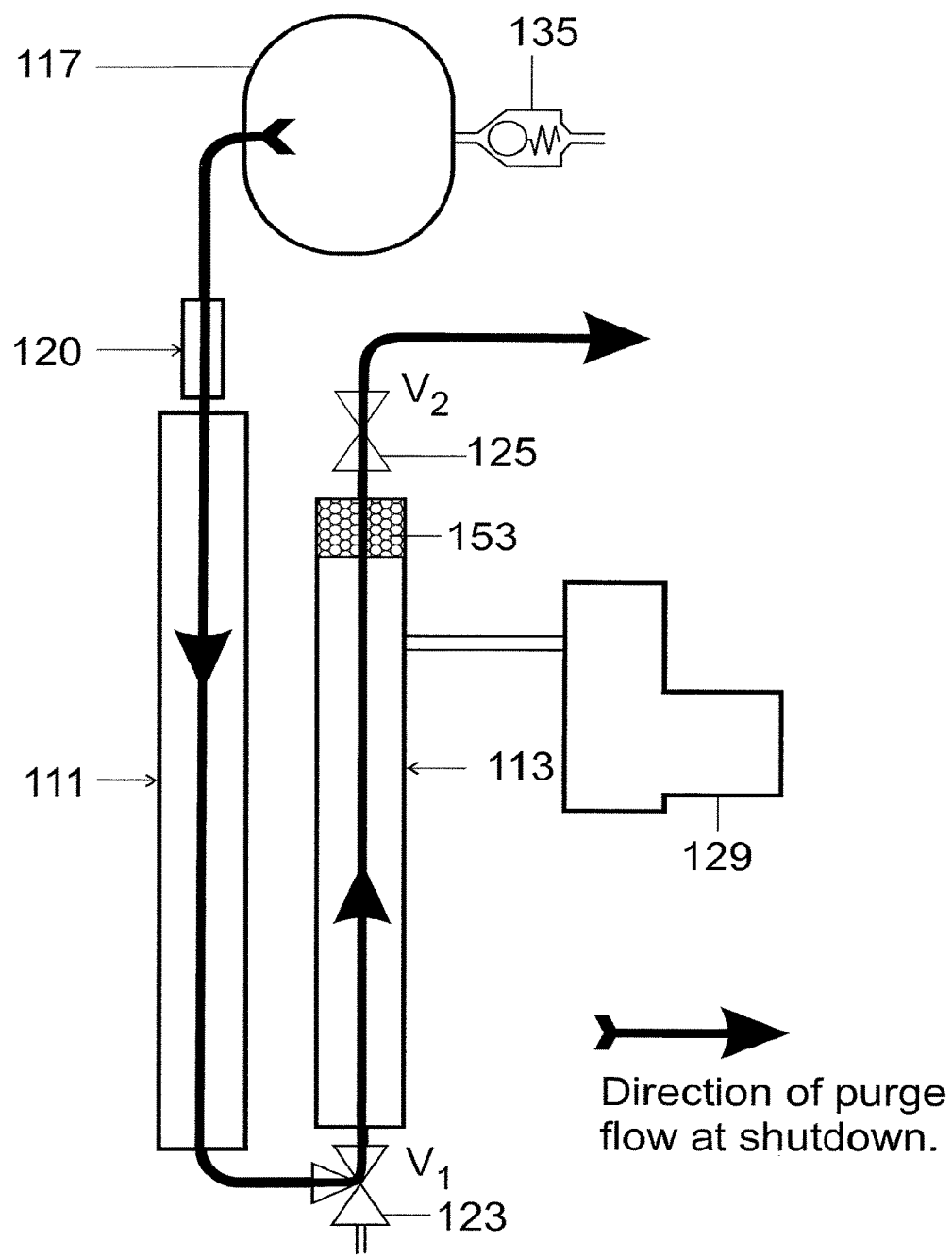
FIG. 10 is a schematic view of the flow of dry product oxygen during the initiation of device shutdown.

When the device is turned off, either by the user in continuous mode, or automatically in bolus mode, the microcontroller conducts a shutdown procedure that is designed to help preserve the integrity of the sieve material and to help prevent moisture contamination. The shut down procedure is as follows: (1) valve 127 closes; (2) compressor 129 ceases operation; (3) valve 123 ceases operation (valve 123 is typically open between air tank 113 and sieve bed 111); (4) purge valve 125 opens for a predetermined period allowing dry product gas from oxygen tank 117 to flood the sieve bed, drive the air from tank 113, and expel some moisture from desiccant 153; (5) valve 125 closes and the sieve bed and communicating passageways and vessels remain filled with ultra dry product gas and are segregated from the external environment. FIG. 10 illustrates the flow of purge gas through the sieve bed, valve, and air tank during the shut down procedure.

In one embodiment the device provides a highly enriched oxygen product at a low flow rate for topical oxygen wound care (TOWT) applications. TOWT is a therapy which consists of covering a wound with an impermeable or semi-permeable covering and then inflating the covering with oxygen. Unlike whole body hyperbaric treatment which must be administered in a facility, this therapy modality allows the patient to retain mobility and to undergo the therapy at home. The supplied oxygen is recognized to contribute to faster healing of burns and diabetic and other types of wounds.

Figure 18:
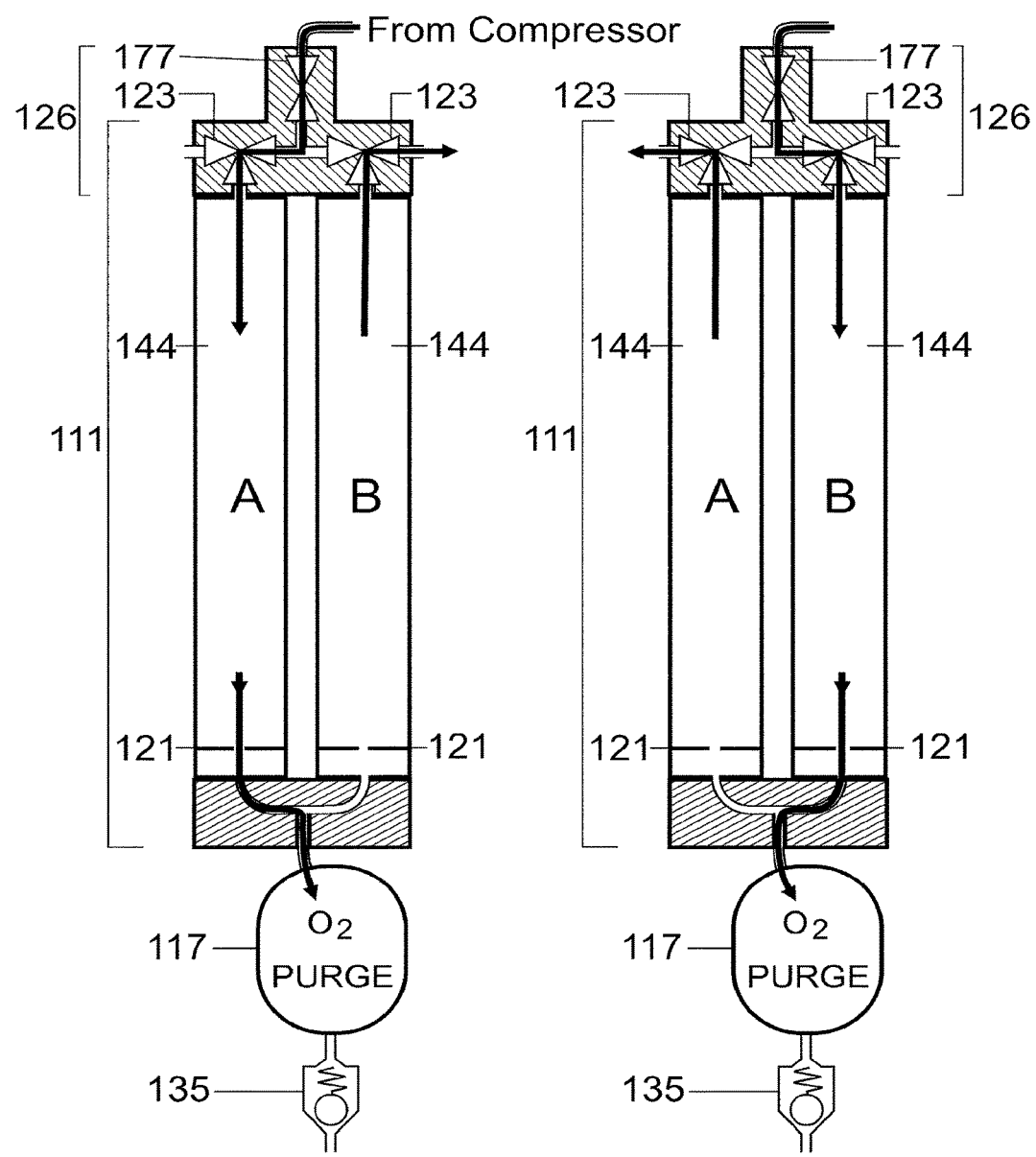
FIG. 18 is a side view and schematic of dual sieve beds operating in the conventional PSA manner.
Figure 19:
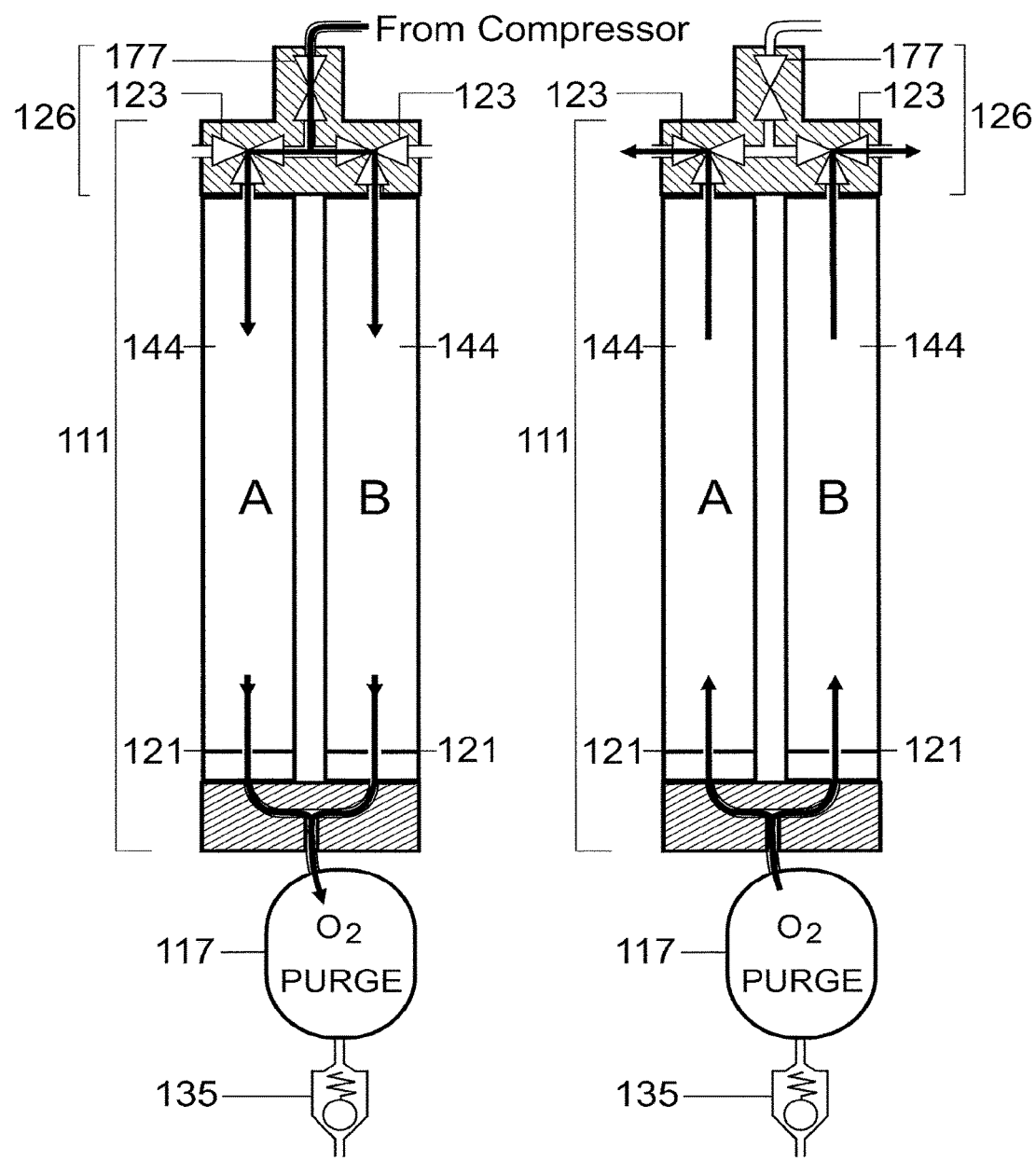
FIG. 19 is a side view and schematic of dual sieve beds operation in a parallel flow mode to produce higher product pressure.

The three modalities presently used for delivering wound care oxygen are hospital oxygen, electrochemically generated oxygen, and via large, often rented, PSA devices. The electrochemical devices produce an ultra low flow (4 ml/hr) of very high purity oxygen which is directed to a tight wound covering. Alternatively, stationary medical respiratory oxygen concentrators capable of delivering 5 L/min of oxygen are used for larger wound coverings. The electrochemical devices have limited utility for large wounds and the medical concentrators are inconvenient and expensive. Also, hospital delivered oxygen limits the patient's mobility and precludes at home treatment. The device of the invention can be configured to deliver about 10-50 ml/min of about 90% purity oxygen. The device uses a single sieve bed and valve, as illustrated in FIG. 6A, or dual sieve beds for higher output as shown in FIGS. 18 and 19. A device has been constructed that uses an inexpensive compressor and only 5 g of adsorbent with a device weight of under one pound. Some practitioners believe that alternating the oxygen flow to the wound covering from high to low with repeating periodicity results in a more effective therapy. The device of the invention can be configured to deliver constant flow, i.e., at about 20-50 ml/min, or repeatedly deliver a large flow, i.e., about 500 ml/min for 4 seconds with a periodicity of once per every 3 minutes. Also the device can be configured to apply sub and supra atmospheric pressure to the wound at a predetermined periodicity. The device can be battery 133 powered as shown in FIG. 2 or the device can be connected to AC mains. The device can be shipped to the patient, as the wound coverings are now, and can be made inexpensive enough to be a single use product. Considerable health care savings are effected by eliminating the oxygen concentrator rental and delivery costs.

Figure 16:
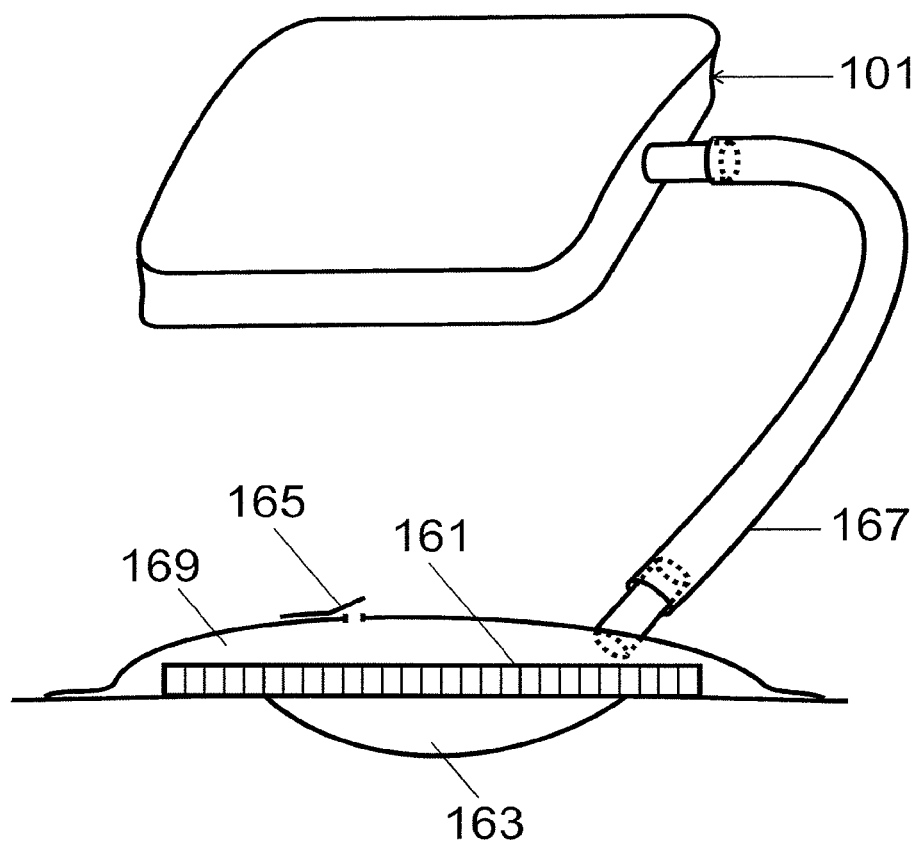
FIG. 16 is an illustration of how the device of the invention may be used for topical oxygen wound therapy.

As shown in FIG. 16, TOWT may be used in combination with a permeable biologically augmented wound covering to further accelerate healing. Biologically augmented materials composed of blood platelets and binder materials have been shown to be effective in the healing of various types of wounds. These materials can be made gas permeable. Again, referring to FIG. 16, the device of the invention 101 produces a flow of oxygen that is delivered through connecting hose 157 to a mostly impermeable covering 159 which is affixed to the patient's skin around the area of the wound 163. Gas permeable biologically augmented material 161 covers the wound and permits oxygen to be made available to the wound. The therapy may be used with or without the use of the biologically augmented material. Oxygen generating device 101 may be strapped to the arm or leg, may be belt mounted, or may be located proximate to the patient. The device 101 can be battery operated for increased patient mobility, or may be AC mains connected.

Figure 7A:
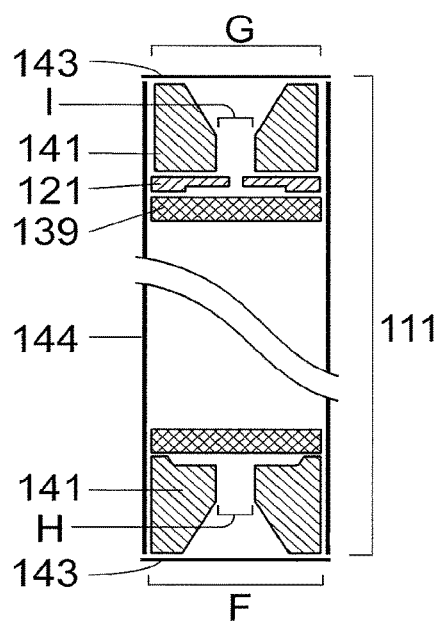
FIG. 7A is a cross-section of sieve bed components where an orifice plate is used as a flow restrictor.
Figure 7B:
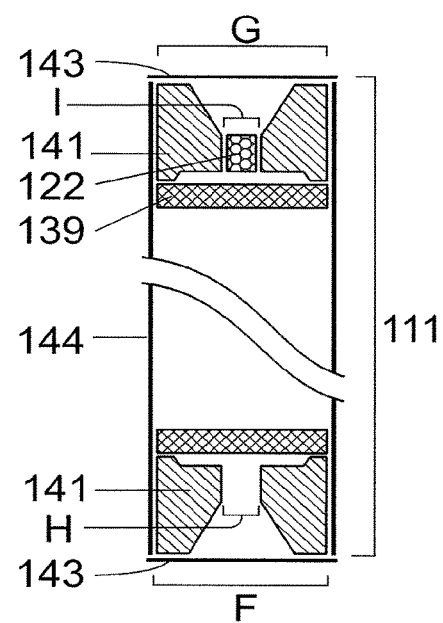
FIG. 7B is a cross-section of sieve bed components where a porous plug is used as a flow restrictor.

FIGS. 7A and 7B illustrate various methods of constructing the sieve bed. Ultra rapid cycle devices have the advantage of using the minimum quantity of adsorbent material, but that also makes them more sensitive to contaminants. One means of mitigating the high sieve bed failure rate associated with smaller sieve beds is to make them easily replaceable. Existing devices require disassembly for adsorbent replacement. The device of the invention incorporates a sieve bed module that can be replaced as easily as a battery is replaced in a consumer electronic device. The receiver ends 141 allow for air tight connection to manifold 126 and sieve bed door 149, as shown in FIG. 8. Pierceable septa 143 seal the sieve bed and protect the adsorbent from moisture contamination until the module is inserted into the device. Upon insertion, conical mechanisms 124 at the manifold end 123 or retainer door end 149 pierce the septum 143 and pneumatic communication is established between the sieve bed module and the appropriate device pneumatic passageway. FIGS. 8, 12A, and 12B illustrate how sealing member 146 forms an airtight seal. These seals may be gaskets or O rings and may be compressible and may be sprint loaded.

The sieve bed(s), as illustrated in FIGS. 6A and 6B, are easily produced and assembled; the details are shown in FIGS. 7A and 7B. Fibrous pad 139 is glued to end 141 and this assembly is pressed and/or glued into one end of cylinder 144. End cap 141 also has distribution channels under the fibrous pad. The assembly is then placed on a scale in a dry box and 5.00 grams of adsorbent, for example, are poured into the sieve bed using a controllable pouring mechanism. The second end cap with fibrous pad and optional restrictor 121, 122 is pressed into cylinder 144 using a predetermined amount of force. Fibrous pads 130 are thus preloaded and the adsorbent beads are locked in place and prevented from moving. Tests conducted over a one year period (8000 hours of operation) showed no attrition of the beads and very little performance degradation due to moisture. It should be understood that a variety of materials may be selected for end caps, restrictor, and fibrous pads, and septa and that various methods may be employed to fasten, affix, and seal these components. For example, fibrous pad 139 may be selected for properties relating to compressibility, permeability, wettability, ability to coalesce moisture, and so forth. Fibrous pads may be constructed of electrospun material containing nano sized alumina particles to form a moisture guard layer.

Now in reference to the product end of the PSA system which, for simplicity and cost reasons, contains no active valving. Some oxygen concentrators use as many as four electrically actuated valves to control product flow. Flow restrictors and a check valve take the place of product end active valving in the device of the invention. Restrictor 120 may be a permanent component of the device or may be part of the replaceable sieve bed as shown in FIG. 7A component 121. Restrictor 120, restricts the flow of product gas during the adsorb period creating the pressure in bed 111 needed for efficient adsorption. Restrictor 120 also serves to limit the flow of purge gas back into the sieve bed during the desorb period. Oxygen purge tank 117 is sized to provide the exact amount of purge gas needed to purge sieve bed 111 during each cycle. Restrictor/check valve 135 permits a portion of the product gas to be stored or used and this gas is not available for purge. Oxygen purge and storage tanks are preferentially integrated into the molded housing pieces that comprise the device case, FIG. 1, component 101, as is air tank 113. Alternatively, these components may be individually constructed tanks which are then connected using miniature hoses. Obviously considerable cost savings accrue when tanks and pneumatic connections are integrated into the two-piece molded case. The cost savings attributable to molded tanks, single PSA valve, single sieve bed, and simplified product end restrictors are especially important for a wound care device which may provide the best health care economics by being a single use device, i.e., the patient discards the oxygen producing device and the wound coverings after the treatment is completed.

When the device is used as a personal oxygen concentrator, a simplified product gas delivery mechanism is required for both direct and cannula mode delivery. Referring to FIGS. 13A and 13B, oxygen product tank(s) 119 connects to valve 127 which is opened when bolus or continuous delivery is required. Valve 127 is connected to nozzle 103 via hose 136. Nozzle door 128 is spring 104 loaded in the closed position and pivots on axle 106. Opening the door exposes the nozzle for cannula 130 connection or direct use while activating valve 127 by switch 102. Alternatively, the nozzle may be a projection placed in a convenient location near the top of the case.

Figure 11:
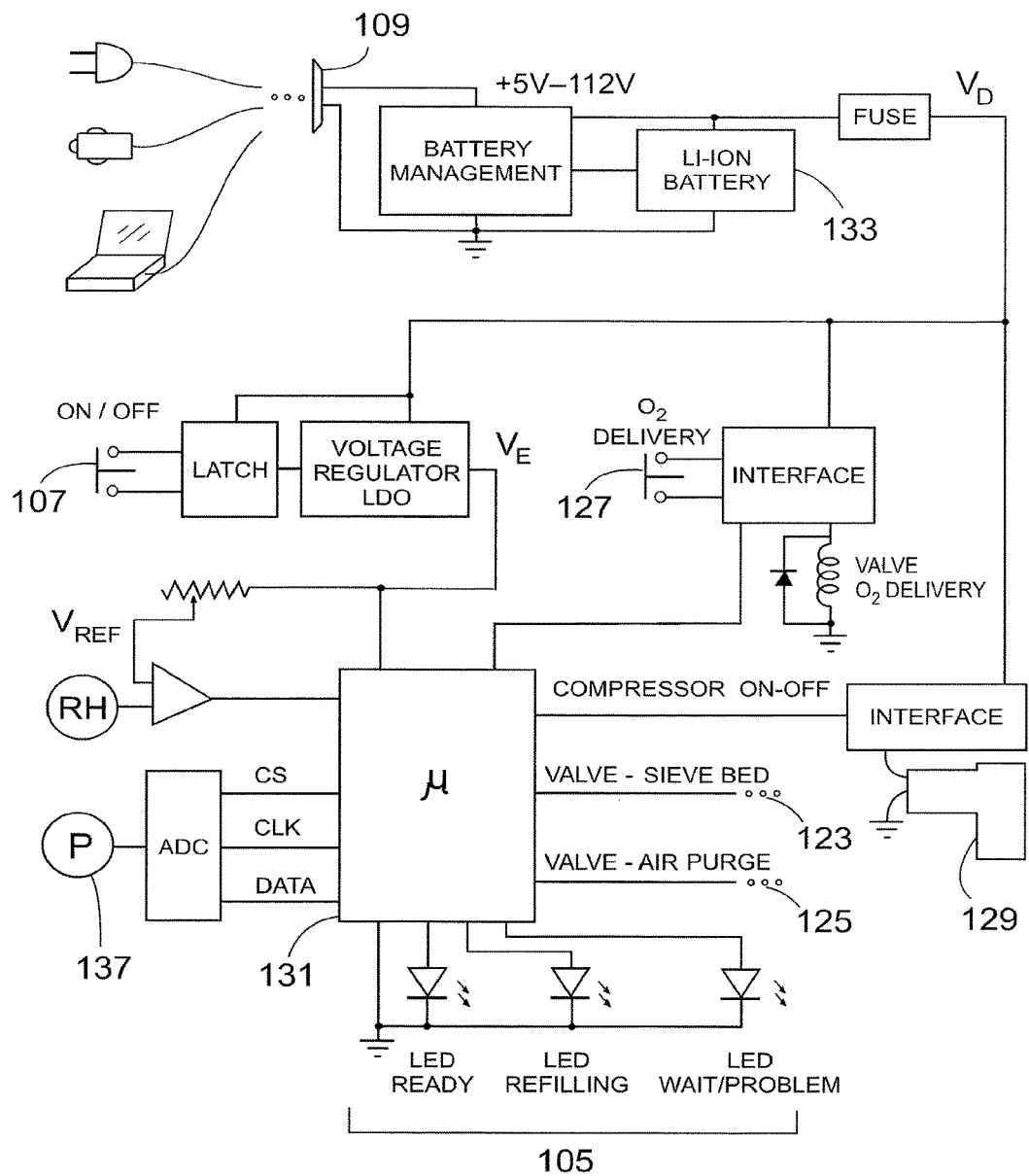
FIG. 11 is a block diagram of one embodiment of the electrical and electronic components of the device of the invention.

Operation as a personal oxygen source also requires some user interface for activation, to select mode of operation, and to report on device status. In FIG. 11, component 109 shows some options (electrical plug, USB, and/or laptop) for charging connections and battery 133 and associated battery management electronics. Switch 107 selects for device on, off, mode of operation, and status display depending on length of time and number of times switch is activated.

Switch 127 activates valve 123 for bolus delivery or for continuous delivery. Electronics 131 controls valve timing shut down procedure, compressor status, and reports status via LEDs 105 or via an alphanumeric readout. Electronics 131 also contains the look-up table which adjusts valve timing in response to a signal from pressure transducer 137.

Figure 13:
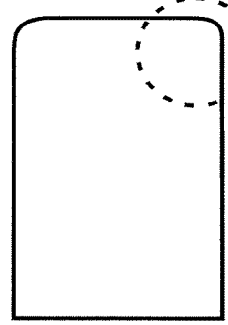
FIG. 13 is a block diagram of the delivery nozzle and cannula connector in one embodiment.
Figure 13A:
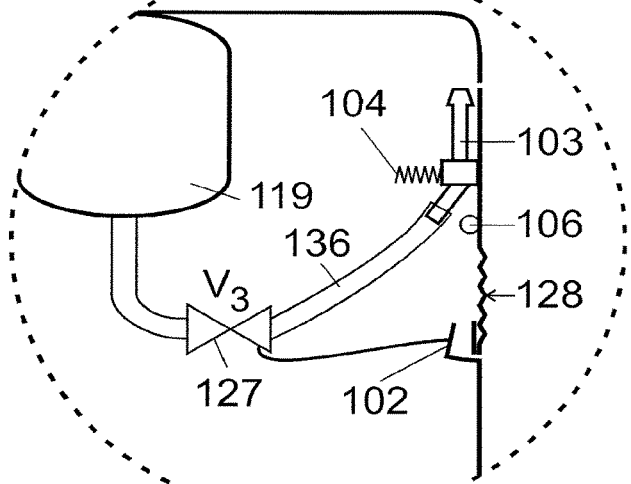
FIG. 13A is a side view and schematic of one embodiment of the delivery nozzle and cannula connector in the closed position.
Figure 13B:
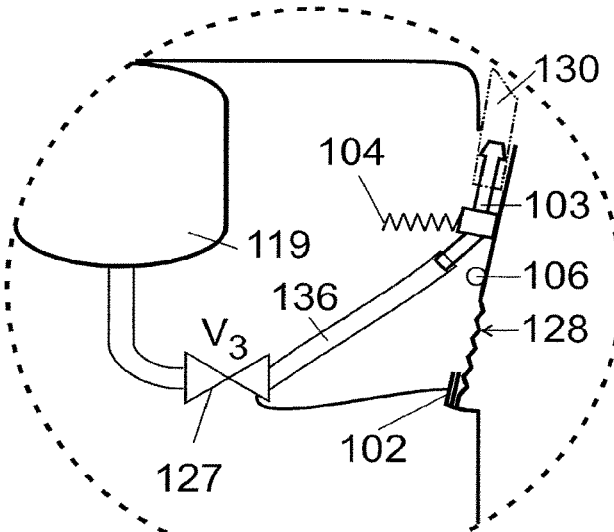
FIG. 13B is a side view and schematic of one embodiment of the delivery nozzle and cannula connector in the open position.
Figure 14:
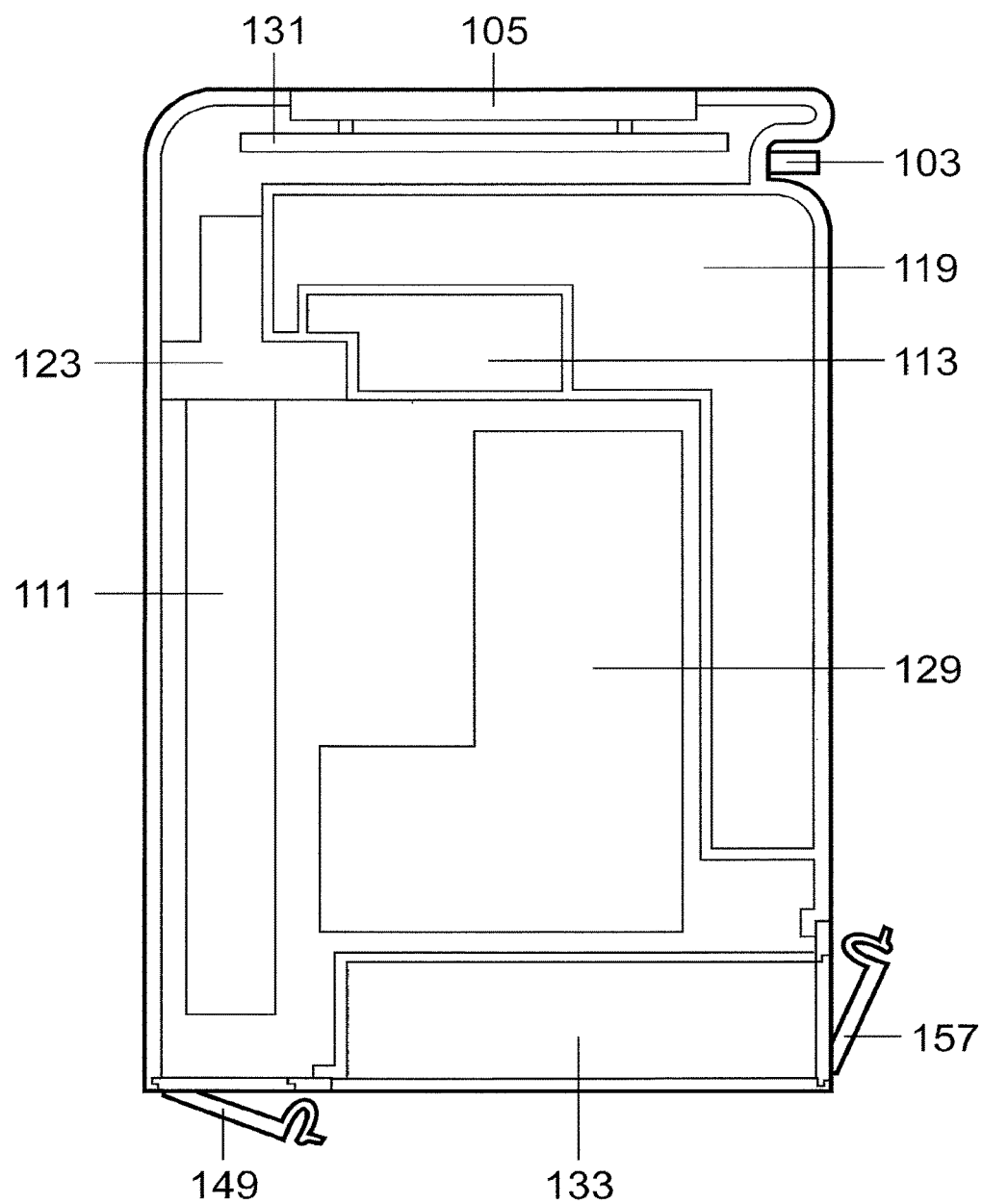
FIG. 14 is a cross-section of a personal oxygen concentrator case which illustrates the position of major components and how gas reservoirs are integrated into the housing.

FIG. 13 shows a cross-section of the personal oxygen concentrator case. Oxygen tanks 119 and 113 have walls formed during the case molding process which define their volume. Interconnections to valves, compressor, and delivery valve are formed by openings in these walls. This design architecture facilitates manufacture, lowers cost, and reduces the mass and volume of the device. Door 149 provides access to the replaceable sieve beds and door 157 provides access to the replaceable batteries.

A series of experiments served to determine the optimal valve timings for different modes of operation. For high purity oxygen production (90%) in continuous mode, adsorb and desorb times are approximately equal. For low purity, high volume product gas (300 ml/min, 32% oxygen purity) production in continuous mode the adsorb time is increased relative to the desorb time. For bolus mode a volume of high purity (90%) oxygen having a volume of 120 ml is produced in 3 minutes 10 seconds by starting with an equal adsorb/desorb valve timing and progressing to a timing where the adsorb time is extended while the desorb time remains constant. This timing methodology produces a volume of oxygen at high purity in the shortest time period as shown in FIG. 5.

Figure 15:
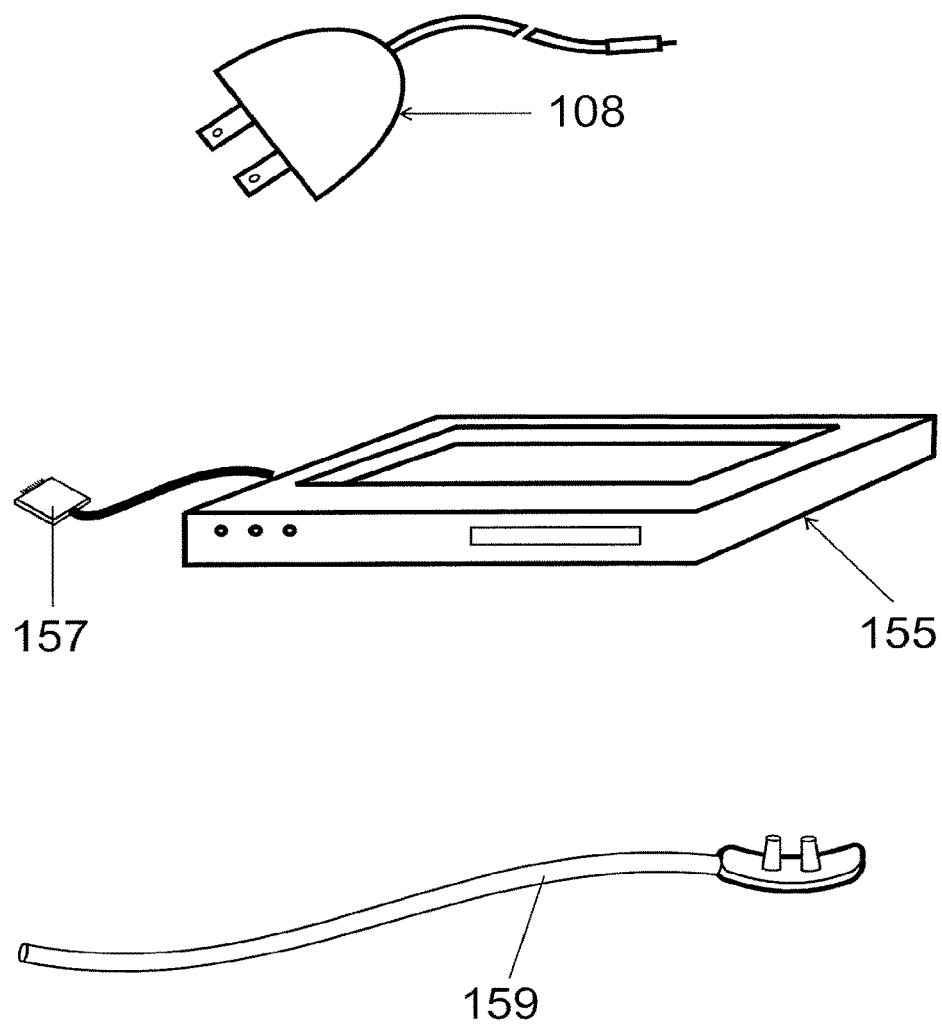
FIG. 15 is an illustration of some of the accessories that may be used with the device of the invention.

FIG. 15 illustrates the various accessories that may be used with the device. Component 108 is an AC mains adapter for providing power to the unit and for charging. Docking station 155 acts as a charge stand and provides computer communication through cable 157. A conserver/cannula 159 is shown.

FIG. 16 Illustrates how the device 101 can be used to deliver OEA to a wound 163 via connecting hose 157. The wound is covered with a semi permeable or non permeable covering 159 which may have an optional pressure relief valve 165. An oxygen permeable biologically augmented material 163 may also be placed directly over the wound or burn and the patient would benefit from both the oxygen delivery and the biologically augmented material therapy modalities.

Figure 17:
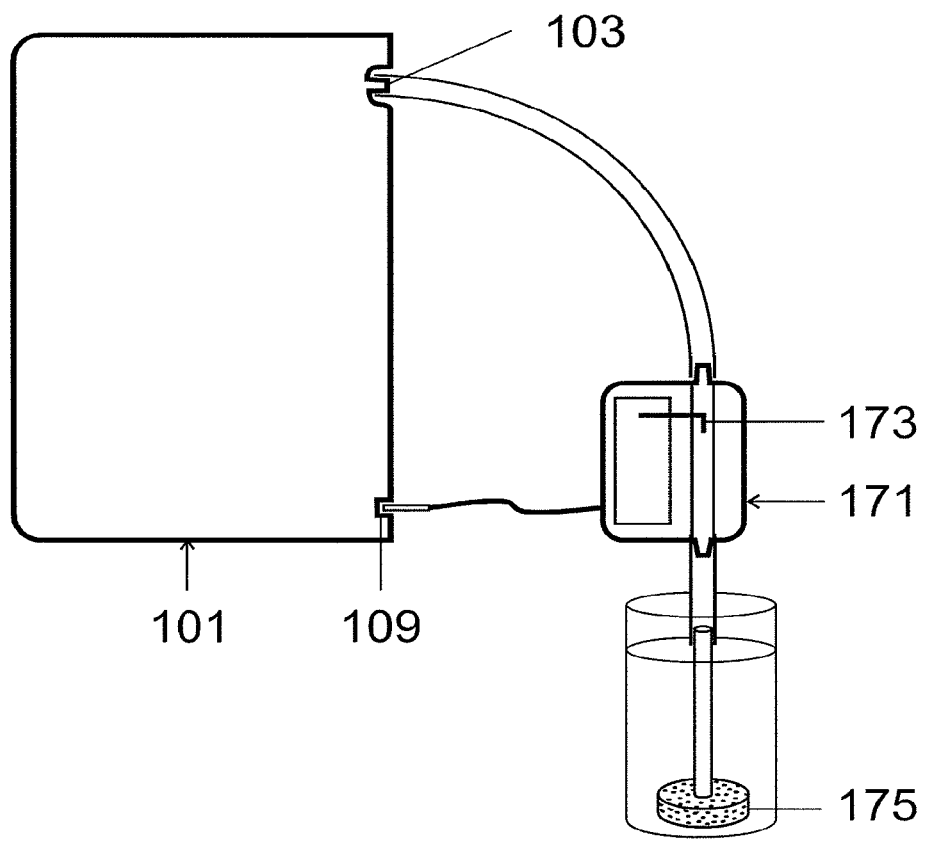
FIG. 17 is an illustration of how the device of the invention may be used to deliver ozone for various purposes.

FIG. 17 illustrates one means of using the device of the invention to deliver ozone which can be used for various purposes i.e. disinfecting wounds or drinking water. High purity oxygen is delivered through nozzle 103 to module 171, which houses a DC to DC converter, which is powered from the charge port 109, and a high voltage electrode 173. The high voltage creates a corona at the electrode point and some of the oxygen passing in the path of the corona is converted into ozone which is then delivered to the diffuser 175. The diffuser is placed in the liquid to be disinfected and the ozone bubbles through the liquid killing any living organisms that it contacts. Alternately the ozone can be delivered to a fresh wound that requires disinfecting. A wound covering similar to that shown in FIG. 16 is used to contain the ozone.

FIGS. 18 and 19 show the operations of a dual sieve bed device having enhanced capabilities. FIG. 18 shows the device operating in typical PSA mode where one bed is adsorbing while the other desorbs. This mode and valve timing is used when high product flow is required at low pressure. FIG. 19 shows the beds operating in parallel flow mode where they essentially act as a single bed. The advantage of this mode of operation is that the adsorb period can be ramped up while the desorb time remains unchanged. This produces a higher product pressure which is useful when a bolus of OEA is being stored in the device. Switching from one mode to the other is accomplished by changing the operations of valves 123 and 127.

In one embodiment, the invention is directed to single sieve bed oxygen enriched air producing PSA devices having a product storage tank, a replaceable sieve bed, an electronically controlled cycle time, a compressed air storage vessel, a product purge gas storage vessel, a larger product storage vessel, a check valve between the two product storage vessels, inlet and exhaust valves, purge valve, delivery valve, replaceable sieve bed with rupture plates on inlet/exhaust and product ends, product end flow restrictors, a compressor, a battery, an electronic control means, a case, user controls, and optional status indicators and filters.

In another embodiment, the invention provides a replaceable dual sieve bed having increased efficiency, inlet/exhaust valves, purge valve, delivery valve, rupture plates, control electronics, case, battery, compressor, associated gas storage vessels, etc In one embodiment of the invention, the device produces and stores a certain amount of OEA having a purity preferentially greater than 80% oxygen at a pressure of less than 300 kPa having a volume at STP of between 40 and 300 ml deliverable to a user by activation of a valve.

In another embodiment, the invention is directed toward a portable battery operated device that can produce and store plus 40% OEA, that can deliver all or a portion of stored OEA at the users discretion, that weighs less that 0.7 kg, that has means for battery charging, and that floods the sieve bed(s) and air passage ways with product gas at shut down in order to maintain adsorbent efficiency and dryness.

In another embodiment, the invention is directed toward portable OEA producing devices that utilize less than 30 grams of 60-160 micro meter diameter spherical nitrogen selective adsorbent beads, that have means for maintaining adsorbent dryness, and that have batteries chargeable via DC power sources, solar energy conversion technology, a computer port, an AC power source, a wireless charging pad, a docking station, or other means, or having a replaceable primary or chargeable battery.

In certain embodiments, the oxygen purge storage vessel 117 is sized to store oxygen-enriched product sufficient to perform the reverse flow purge function (exhausting desorbed nitrogen) during the desorb cycle, but not so much oxygen-enriched product that it is unnecessarily expelled through the pressure swing adsorption (PSA) valve 123.

In certain embodiments, the oxygen purge storage vessel 117 is sized to store dry oxygen-enriched product sufficient to partially or fully purge the sieve bed(s), head space, manifolds, valves, and air storage vessel 113 through the system purge valve 125 during the shutdown procedure.

In certain embodiments, an algorithm is stored in a microprocessor or microcontroller that relates the pressure in the oxygen bolus storage vessel 119 with the length of the adsorb portion of the PSA cycle. Preferably, the cycle timing begins with an equal adsorb and desorb period, and then the adsorb period lengthens as the pressure in the oxygen bolus storage vessel 119 increases (as measured by the pressure sensor 137). This results in a more rapid pressure build-up in the oxygen bolus storage vessel 119 than that which would occur if the adsorb and desorb periods were to remain equal, since an adsorbent has greater capacity at higher pressures. Therefore, breakthrough does not occur, even at the extended adsorb times.

In certain embodiments, a desiccant is positioned in the air storage vessel. The desiccant helps to remove water vapor from the incoming air and traps any liquid water that accumulates in the device. In preferred embodiments, the desiccant is placed such that the ultra-dry oxygen-enriched air that is used to purge the moist air from the device during shutdown passes directly through the desiccant, driving any accumulated moisture out of the desiccant in the moisture control unit and carrying it out of the device. In certain embodiments, the moisture control unit 153 may comprise an aluminum oxide-derived product. In certain embodiments, the moisture control unit or dryer 153 may comprise a functionally graded material In one embodiment, an antimicrobial substance, such as a biocide bead, may be present in the air storage vessel 113; said oxygen purge storage vessel 117; said oxygen bolus storage vessel 119 having a pressure sensor 137; or some combination thereof, to minimize or prevent the accumulation and/or proliferation of harmful pathogens.

The devices, systems, and methods of the various embodiments permit delivery of a bolus of oxygen-enriched air in a short period of time of high purity and under moderate pressure, and also provides sufficient flow restriction that, in continuous mode, maintains a predetermined oxygen content. Valve timing may alter when changing from bolus to continuous mode. Due to their high efficiency and small size, the devices of the various embodiments may be hand-held or pocket-held. Furthermore, the methods of the various embodiments permit use of single adsorbent bed devices and single pressure swing adsorption (PSA) valves, far less expensive to produce than conventional devices.

In certain embodiments, the air storage vessel 113, the oxygen purge storage vessel 117, and the oxygen bolus storage vessel 119 may form a part of the case, which may be injection molded. In certain embodiments, the valves and restrictors between the air storage vessel 113, the oxygen purge storage vessel 117, and the oxygen bolus storage vessel 119 may form part of the walls or the partitions that define the vessels.

Oxygen Purge Storage Vessel (117)

The oxygen purge storage vessel 117 is needed for the device to operate because it provides the necessary amount of purge oxygen needed to move adsorbed nitrogen out of the sieve bed during the desorption phase. It is also necessary for providing dry oxygen to remove all moist air from the device at shutdown, which occurs after each pressure build cycle in bolus mode and after any period of operation in continuous mode.

Pressure Sensor (137)

Figure 4A:
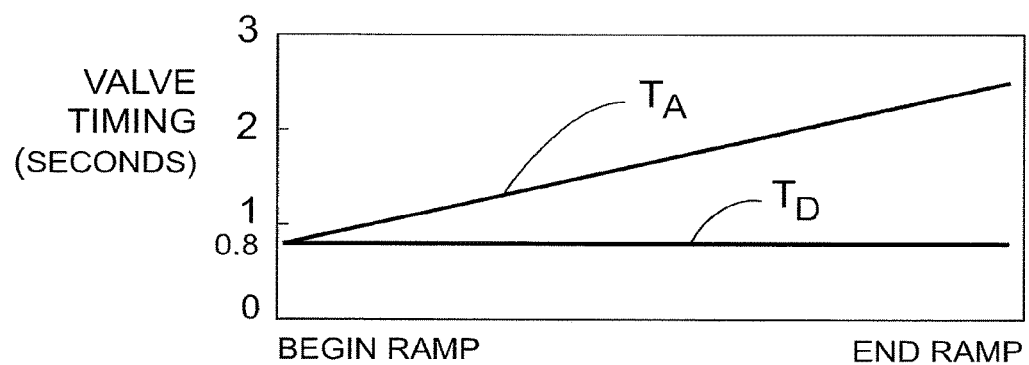
FIG. 4A is a graph showing how adsorption valve timing changes from beginning to end of pressure ramp-up.
Figure 4B:
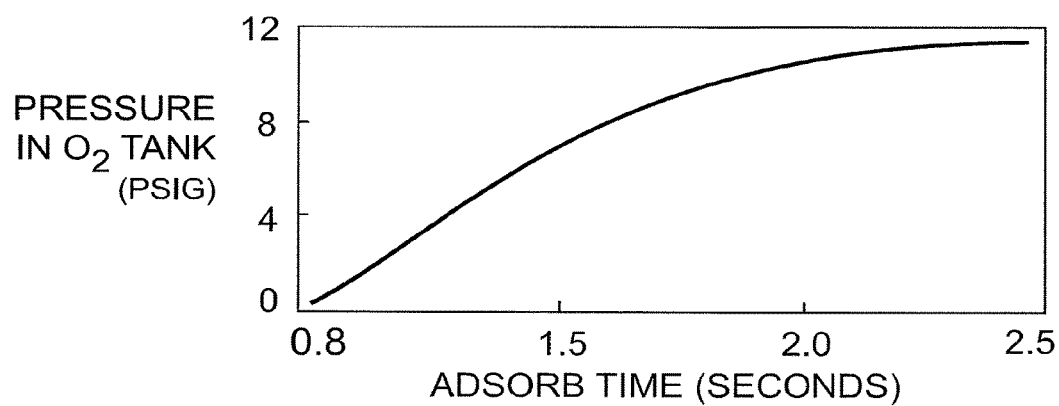
FIG. 4B is a graph showing how pressure in oxygen storage tank 119 increases as adsorption cycle time progresses from beginning to end of ramp-up.
Figure 4C:
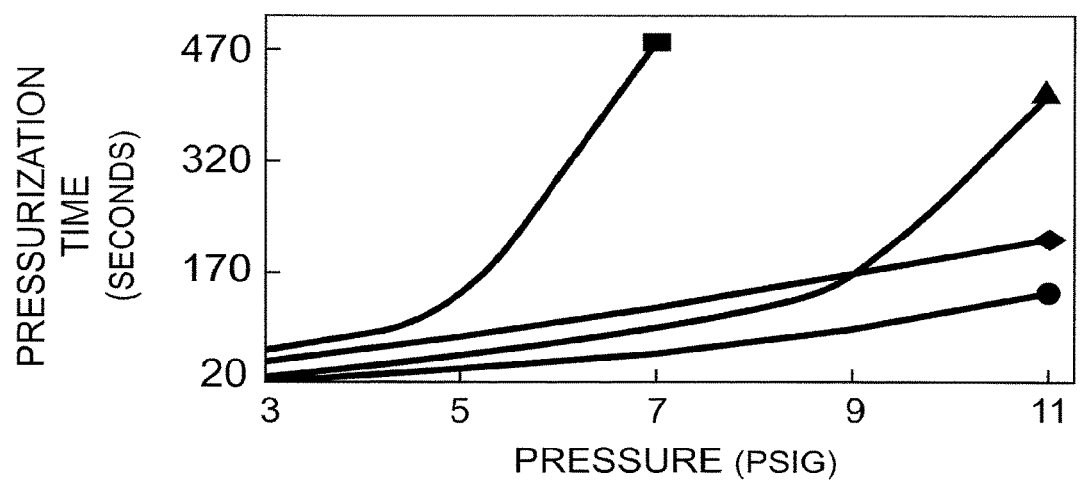
FIG. 4C is a graph showing adsorb time versus product pressure.

The pressure sensor serves at least three purposes in the device of the invention. First, it measures the pressure in the oxygen bolus storage vessel 119 and sends a signal to a microcontroller that changes the timing of the pressure swing adsorption valve, as needed. As the pressure increases, the adsorption timing gets longer (as shown in FIG. 4C). The microcontroller holds the algorithm that defines this relationship. This makes better use of the capacities of the adsorbent material and allows for faster pressure build in the oxygen bolus storage vessel 119 because the device spends more time delivering product gas than desorbing. Second, at a predetermined pressure, the compressor 129 shuts off and the device goes into standby if it is in the bolus delivery mode. If it is in continuous mode, the compressor 129 keeps running because it does not achieve a predetermined pressure. Finally, the pressure sensor 137 can indicate that there is a system malfunction, i.e., sieve bed is contaminated if the oxygen bolus storage tank 119 reaches pressure in too short a period of time or that the filter is plugged if the oxygen bolus storage tank 119 reaches pressure in too long a period of time.

In certain embodiments, the sieve bed of the device is coiled, folded, or otherwise modified to allow the adsorbent column to have the required linear length for efficient separation while fitting into a much smaller space.

In certain embodiments, the invention is directed to a method of packing the sieve bed, such that no springs are required. The beds are compacted during filling by vibration or other methods to ensure that there are no void spaces in the adsorbent column, and an end cap or plug is pressed into place to constrain the sieve material. The plug contains necessary air diffusion channels and has an attached filter/pad that is made of a pliable porous material such as fiberglass mat, foam rubber, or other material.

In certain embodiments, the invention is directed to a method of controlling flow in and out of the product end of the sieve bed(s), such that orifices are used instead of check valves, mechanical valves, or electromechanical valves. This simplifies operation and keeps costs low.

In certain embodiments, the oxygen reservoirs of the device function such that there are two reservoirs in series. A first reservoir, preferably of about 7 cubic centimeters in volume, and a second reservoir, preferably of about 80 to 85 cubic centimeters in volume. The reservoirs are separated by a check valve/restrictor; the first reservoir allows for a small volume of oxygen-enriched gas to be used as a sweep gas for the sieve bed, and the second, larger reservoir stores oxygen-enriched gas under pressure for delivery to the user.

In certain embodiments, the device operates such that the device builds until a certain pressure is achieved in the second oxygen tank, then enters a standby or rest mode until such time as the oxygen in the tank is delivered to the user or the pressure is otherwise reduced to a predetermined setting.

In certain embodiments, the invention is directed to method for keeping water contamination to a minimum when the device is shutdown, such that ultra dry (<1 ppm water) oxygen-enriched air from the first reservoir is bled back through the system to purge the moist air from it. The flow of oxygen enriched air is controlled by an electromechanical valve that is activated by a microcontroller during the shutdown sequence.

In certain embodiments, an algorithm is stored in a microcontroller or microprocessor such that a relationship is made between the pressure in the second oxygen tank (product storage tank) and the length of the adsorb portion of the PSA cycle. The cycle timing begins (preferably) as equal adsorb and desorb times, and then the adsorb period lengthens as the storage tank increases, resulting in a more rapid pressure build up in the storage tank than that which would occur if the adsorb and desorb times were to remain equal. An adsorbent has greater capacity at higher pressures and therefore breakthrough does not occur even at the extended adsorb time.

In certain embodiments, the first oxygen storage tank is sized to store sufficient product gas such that adequate product gas is available to perform the reverse flow purge function during the desorb cycle, but not so much product gas that the product gas is expelled through the exhaust during the desorb cycle.

In certain embodiments, the first oxygen storage tank is sized to store sufficient dry product gas such that sufficient product gas is available to partially or completely purge the sieve bed, head space, manifolds, valves, and air storage tank during the shutdown procedure.

In certain embodiments, the air, first and second oxygen storage tanks are part of the injection molded case and valves between the tanks may form part of the walls or partitions that define these tanks.

In certain embodiments, the device may operate in burst mode where the user activates a valve that releases the stored bolus of highly oxygen enriched OEA.

In certain embodiments, the device may operate in continuous mode where moderately oxygen enriched OEA is delivered continuously through a flexible tube to the vicinity of the users mouth or nose.

In certain embodiments, the device may operate in conserver mode where moderately oxygen enriched OEA is delivered during inhalation through a flexible tube to the vicinity of the users mouth or nose.

In certain embodiments, a biocide bead may be incorporated into the air and/or oxygen storage tanks to prevent the build up of harmful organic pathogens.

In certain embodiments, the sieve bed(s) may be replaceable.

In certain embodiments, the device may include a battery that is chargeable via a computer connection, a docking station, a wireless charge pad, a house current charger, a solar cell, an automotive charger, or any other convenient charging means.

In certain embodiments, the device may include, as an accessory, a disposable oxygen indicator that measures the percent of oxygen present in the device output OEA.

In certain embodiments, the device may have a carrying case, cover, handle or clip, or bag.

In certain embodiments, the device may weigh less than about 450 grams, preferably less than about 350 grams.

In certain embodiments, the device may include compressor speed settings that allow the device to operate in a noise mode that is appropriate to the existing environmental noise level.

In certain embodiments, the device may include a docking station or computer interface that performs diagnostic functions.

In certain embodiments, the device may have a removable battery pack

In certain embodiments, the invention is directed to a portable air separation device weighing less than one lb that can deliver +85% purity oxygen enriched air at a flow rate of at least 60 ml per minute for at least 90 minutes that contains its own power source that can be used for topical oxygen wound/burn therapy.

In certain embodiments, the invention is directed to a portable air separation device weighing less that one lb that can deliver oxygen for at least 90 minutes that contains its own power source to a distribution network contained in a shoe, glove, or other body part covering for the purpose of providing topical oxygen therapy.

It will be apparent to those skilled in the art that various modifications and variations can be made in the present invention and specific examples provided herein without departing from the spirit or scope of the invention. Thus, it is intended that the present invention cover the modifications and variations of this invention that come within the scope of any claims and their equivalents.

EXAMPLES

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

Example 1

A portable device is designed that employs a single molecular sieve bed which measures 12 mm in diameter and 80 mm in length, contains approximately 5 grams of 80 to 140 micro meter diameter Lithium exchanged molecular sieve beads, and has pre-loaded piercable ends. A battery operated compressor delivers air to a three way PSA valve at 1.5 liters per minute and 180 kPa pressure. The valve alternately pressurizes and depressurizes the sieve bed at a beginning timing of 0.8 sec adsorb and 0.8 sec desorb. An oxygen enriched product is delivered, through an orifice to a 20 cm3 volume purge vessel, then through a check valve/restrictor to an 80 cm3 volume product storage vessel. As the product storage vessel pressure increases, the adsorb time increases until product storage pressure is 180 kPa and adsorb time is 2.5 seconds. An algorithm generates lookup tables that are stored in a microcontroller and the microcontroller accepts data from a storage vessel pressure transducer to generate the relevant adsorb time signal. A lithium-ion battery provides 24 watt hours of energy, which is sufficient for 4.8 hours of continuous operation at a delivery rate of 400 ml per minute at 32% oxygen content, or to provide 115 boluses of 90% purity OEA at a volume of 120 ml per bolus.

The device components are contained in a case which measures approximately 30 mm×100 mm×160 mm with a weight of about 400 grams. A user interface provides data concerning oxygen purity, battery condition, and sieve bed condition. A push button operated door provides access to a delivery nozzle while simultaneously opening a delivery valve. When a cannula is attached to the nozzle the door remains open and a continuous supply of OEA is delivered. The batteries and sieve bed are removable and replaceable through appropriate closable doors. Battery chargers for various power sources are provided. Various delivery modalities are anticipated including cannula, nozzle, head piece, mask, liquid oxygenator, and wound care covering. A carrying pouch may also be provided.

Example 2

A device is designed that uses 5 grams of adsorbent in a single sieve bed, that cycles at 0.8 seconds desorption and ramps to 1.5 seconds adsorb, and that is either battery or AC mains powered through a transformer. The device uses a 7000 rpm diaphragm compressor which weighs 47 grams, a three way inlet exhaust valve, a purge valve, and a microcontroller to provide timing signals to the valves 20 ml per minute of OEA at plus 85% oxygen content is delivered through a flexible tube to a wound covering. The device components are located in a suitable case and the device weighs less than 200 grams. The device is provided to a patient as part of a wound care kit which also contains several wound coverings and adhesive attachment means as well as flexible tubing to connect the oxygen supply to the wound covering.

Example 3

A device is designed that uses 5 grams of adsorbent in a single sieve bed that is cycled at a timing of 0.8 seconds desorption and 0.8 seconds adsorption. A flow rate of 400 ml per minute at 32% oxygen content is produced and delivered through a flexible tube to a nose piece, head piece, or mask that allows a user to inhale the product gas. The device contains a compressor that operates at 3300 rpm, 150 kPa, and at a flow rate of 2.5 liters per minute air at standard temperature and pressure. The device is powered by a 23 watt hour, 7.4 volt lithium-ion battery that can operate the device for 4.6 hours. The user is provided with a device that weighs less than one pound and delivers sufficient oxygen to assist lung function for persons at high altitudes, in polluted environments, or in exercise situations. The battery and sieve bed are easily replaceable by the user. An optional replaceable air filter may be included. The device may also include a conserver that causes the device to deliver oxygen only when the user inhales. The conserver effectively triples the amount of oxygen delivered to the user's lungs.

Example 4

A device is designed based on the invention that uses a pressure sensor. The pressure sensor serves at least three purposes in the device of the invention. First, it measures the pressure in the oxygen bolus storage vessel (119) and sends a signal to a microcontroller, which is integrated into electronics package 131 that changes the timing of the pressure swing adsorption valve, as needed. As the pressure increases, the adsorption timing gets longer (as shown in FIG. 4C). The microcontroller holds the algorithm that defines this relationship. This makes better use of the capacities of the adsorbent material and allows for faster pressure build in the oxygen bolus storage vessel 119 because the device spends more time delivering product gas than desorbing. FIG. 5 illustrates the effect of changing the adsorb timing. Second, at a predetermined pressure, the compressor 129 shuts off and the device goes into standby if it is the bolus delivery mode. If it is continuous mode, the compressor 129 keeps running because it does not reached a predetermined pressure. Finally, the pressure sensor 137 can show that there is a system malfunction, i.e., sieve bed is contaminated if the oxygen bolus storage tank 119 reaches pressure in too short a period of time or that the air filter is plugged if the oxygen bolus storage tank 119 reaches pressure in too long a period of time.

The sieve bed of the device may be coiled, folded, or otherwise modified in order to allow the adsorbent column to have the required linear length for efficient separation while fitting into a much smaller space.

The sieve bed is filled with adsorbent such that no springs are required. The beds are compacted during filling by vibration or other methods to ensure that there are no void spaces in the adsorbent column, and an end cap or plug is pressed into place to constrain the bed. The plug contains necessary air diffusion channels and has an attached filter/pad that is made of a pliable porous material such as fiberglass mat, foam rubber, or other material.

Product flow in and out of the product end of the sieve bed(s) is controlled such that orifices are used instead of check valves, mechanical valves, or electromechanical valves. This simplifies operation and keeps costs low.

The device is designed such that there are two oxygen reservoirs in series. The first reservoir is preferably of about 7 cubic centimeters in volume, and the second reservoir is preferably of about 80 to 85 cubic centimeters in volume. The first oxygen storage tank is sized to store sufficient dry product gas such that sufficient product gas is available to partially or completely purge the sieve bed, head space, manifolds, valves, and air storage tank during the shutdown procedure The reservoirs are separated by a check valve/flow restrictor. The second, larger reservoir stores oxygen-enriched gas under pressure for delivery to the user.

Sieve adsorbent contamination is kept to a minimum by using a shutdown procedure such that ultra dry (<10 ppm water) oxygen-enriched air from the first reservoir is bled back through the system to purge the moist air from the sieve bed and air storage vessel. The flow of oxygen enriched air is controlled by an electromechanical valve that is activated by the microcontroller during the shutdown sequence.

When ranges are used herein for physical properties, such as molecular weight, or chemical properties, such as chemical formulae, all combinations, and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

| Component Number | Component Name |
| --- | --- |
| 100 | Docking Station |
| 101 | Case |
| 102 | Electrical Valve Switch (optional) |
| 103 | Oxygen Delivery Nozzle |
| 104 | Retaining Spring |
| 105 | Status Display |
| 106 | Pivot |
| 107 | Controls |
| 108 | Charging Device |
| 109 | Power/Charge Port |
| 111 | Sieve Bed Assembly, Single or Folded |
| 113 | Air Storage Vessel |
| 115 | Air Delivery Channel |
| 117 | Oxygen Purge Storage Vessel |
| 119 | Oxygen Bolus Storage Vessel |
| 120 | Restrictor Assembly |
| 121 | Restrictor, Orifice |
| 122 | Restrictor, Porous |
| 123 | V1, PSA Valve |
| 124 | Piercing Mechanism |
| 125 | V2, System Purge Valve |
| 126 | PSA Valve Manifold |
| 127 | V3, Delivery Valve |
| 128 | Nozzle Door |
| 129 | Compressor |
| 130 | Cannula |
| 131 | Electronics |
| 133 | Battery |
| 135 | Purge/Bolus Check Valve |
| 136 | Connecting Hose |
| 137 | Pressure Sensor |
| 139 | Sieve Pad |
| 141 | End Cap |
| 143 | Rupture Plate |
| 144 | Sieve Housing Cylinder |
| 145 | Dual Bed Product Manifold |
| 146 | Gasket |
| 147 | Product Delivery Channel |
| 149 | Sieve Access Door |
| 151 | Retaining Screw |
| 153 | Dryer media |
| 155 | Docking Station |
| 157 | Computer Interface |
| 159 | Conserver |
| 161 | Permeable Biologically Augmented Material |
| 163 | Wound |
| 165 | Pressure Relief Valve |
| 167 | Hose |
| 169 | Wound Cover |
| 171 | DC - DC Converter |
| 173 | High Voltage Electrode |
| 175 | Diffuser |
| 177 | V4, Compressor Valve |

What is claimed is:

1. A method of purging contaminants from a device for oxygen enrichment, comprising:

compressing in said device an ambient air flow comprising oxygen and nitrogen to form a compressed air flow;

transporting said compressed flow through at least one adsorbent bed and adsorbing at least a portion of said nitrogen in said at least one adsorbent bed to form an oxygen-enriched gas flow;

removing said oxygen-enriched gas flow to form an oxygen-enriched product;

transporting said oxygen-enriched product to a first vessel; and purging said adsorbent bed using said oxygen-enriched product in said first vessel upon shutdown of said device to remove said contaminants without permitting entry of material from the external environment;

wherein said oxygen-enriched product passes through an orifice between said first vessel and said at least one adsorbent bed; and wherein said oxygen-enriched product does not pass through a check valve, mechanical valve, or electromechanical valve between said first vessel and said at least one adsorbent bed.

2. A method of purging contaminants from a device for oxygen enrichment, comprising:
compressing in said device an ambient air flow comprising oxygen and nitrogen to form a compressed air flow;
transporting said compressed flow through an air delivery manifold and then at least one adsorbent bed and adsorbing at least a portion of said nitrogen in said adsorbent bed to form an oxygen-enriched gas flow and adsorbed nitrogen;
removing said oxygen-enriched gas flow to form an oxygen-enriched product;
transporting said oxygen-enriched product to a first vessel;
optionally, desorbing from said adsorbent bed said adsorbed nitrogen and exhausting said nitrogen; and
purging said at least one adsorbent bed and said air delivery manifold using said oxygen-enriched product in said first vessel upon shutdown of said device to remove said contaminants without permitting entry of material from the external environment;
wherein said oxygen-enriched product passes through an orifice between said first vessel and said at least one adsorbent bed; and
wherein said oxygen-enriched product does not pass through a check valve, mechanical valve, or electromechanical valve between said first vessel and said at least one adsorbent bed.

3. The method of claim 2,
wherein said contaminant is moisture.

4. The method of claim 2,
wherein said air delivery manifold is an air storage vessel.

5. The method of claim 2,
wherein said air delivery manifold comprises a dryer material.

6. A method of purging contaminants from a device for oxygen enrichment, wherein said device comprises:
a compressor (129);
an air storage vessel (113) having a system purge valve (125);
at least one pressure swing adsorption unit (111) comprising at least one adsorbent bed;
an oxygen purge storage vessel (117);
an oxygen bolus storage vessel (119);
a first passageway (A) connecting said compressor (129) and said air storage vessel (113);
a second passageway (B) connecting said air storage vessel (113) and said pressure swing adsorption unit (111);
a third passageway (C) connecting said pressure swing adsorption unit (111) and said oxygen purge storage vessel (117);
a fourth passageway (D) connecting said oxygen purge storage vessel (117) and said oxygen bolus storage vessel (119);
a first pressure swing adsorption valve (123) associated with said second passageway (B), pressure swing adsorption unit (111), and exhaust to ambient pressure;
wherein said first pressure swing adsorption valve is a three-way valve or two two-way valves;
a restrictor assembly (120) positioned between said pressure swing adsorption unit (111) and said oxygen purge storage vessel (117) and connected to said third passageway (C);
wherein said restrictor assembly is an orifice;
a check valve/restrictor (135) positioned between said oxygen purge storage vessel (117) and said oxygen bolus storage vessel (119); and
a delivery valve (127) positioned between said oxygen bolus storage vessel (119) and a delivery nozzle (103);
said method comprising the steps of:
operating said device to store product gas in said oxygen purge storage vessel (117);
closing said delivery valve (127);
ceasing operation of said compressor (129);
opening said system purge valve (125) for a predetermined period of time to the atmosphere thereby permitting said product gas stored in said oxygen purge storage vessel (117) to flow through said passageway C, said at least one pressure swing adsorption unit (111), said passageway B and said air storage vessel (113) out to the atmosphere through said system purge valve (125) to at least partially purge said device and expel at least one contaminant without permitting entry of material from the external environment;
wherein said product gas passes through said orifice between said oxygen purge storage vessel and said pressure swing adsorption unit; and
wherein said product gas does not pass through a check valve, mechanical valve, or electromechanical valve between said oxygen purge storage vessel and said pressure swing adsorption unit.

7. The method of claim 6, further comprising the step of:
closing said system purge valve (125) to retain said product gas in said device;
wherein said product gas is dry.

8. The method of claim 6,
wherein said product gas is oxygen-enriched air having less than 1 ppm water.

9. The method of claim 6,
wherein said product gas retained in said device is supra atmospheric.

10. The method of claim 6,
wherein said system purge valve (125) is placed adjacent to said first passageway (A).

11. The method of claim 6,
wherein said contaminant is moisture.

12. The method of claim 6,
wherein said steps of closing said delivery valve, ceasing operation of said compressor, and opening said system purge valve happen substantially simultaneously.

13. The method of claim 6,
wherein said steps of closing said delivery valve and ceasing operation of said compressor happen in any order.

14. The method of claim 6,
wherein said at least one pressure swing adsorption unit (111) comprising two adsorbent beds.

* * * * *